US012070398B2

(12) United States Patent
Lenzi et al.

(10) Patent No.: US 12,070,398 B2
(45) Date of Patent: Aug. 27, 2024

(54) VARIABLE TRANSMISSION FOR ASSISTIVE PROSTHESIS DEVICE

(71) Applicant: UNIVERSITY OF UTAH RESEARCH FOUNDATION, Salt Lake City, UT (US)

(72) Inventors: Tommaso Lenzi, Salt Lake City, UT (US); Minh Tran, Salt Lake City, UT (US); Marco Cempini, Miami Beach, FL (US)

(73) Assignee: University of Utah Research Foundation, Salt Lake City, UT (US)

( * ) Notice: Subject to any disclaimer, the term of this patent is extended or adjusted under 35 U.S.C. 154(b) by 512 days.

(21) Appl. No.: 17/269,627

(22) PCT Filed: Aug. 28, 2019

(86) PCT No.: PCT/US2019/048489
§ 371 (c)(1),
(2) Date: Feb. 19, 2021

(87) PCT Pub. No.: WO2020/047043
PCT Pub. Date: Mar. 5, 2020

(65) Prior Publication Data
US 2021/0338458 A1 Nov. 4, 2021

Related U.S. Application Data

(60) Provisional application No. 62/723,810, filed on Aug. 28, 2018, provisional application No. 62/723,818, filed on Aug. 28, 2018.

(51) Int. Cl.
*A61F 2/64* (2006.01)
*A61B 5/107* (2006.01)
(Continued)

(52) U.S. Cl.
CPC ............ *A61F 2/644* (2013.01); *A61B 5/1071* (2013.01); *A61B 5/112* (2013.01); *A61F 2/64* (2013.01);
(Continued)

(58) Field of Classification Search
None
See application file for complete search history.

(56) References Cited

U.S. PATENT DOCUMENTS 4,483,194 A 11/1984 Rudolf
4,762,006 A 8/1988 Asakawa et al.
(Continued)

FOREIGN PATENT DOCUMENTS

CN 101336849 A 1/2009
CN 102204918 A 10/2011
(Continued)

OTHER PUBLICATIONS

International Search Report and Written Opinion dated Nov. 14, 2019 for PCT/US2019/048489.
(Continued)

*Primary Examiner* — David H Willse
(74) *Attorney, Agent, or Firm* — Ballard Spahr LLP

(57) ABSTRACT

The present disclosure describes transmission systems for use in artificial joints of assistive devices, such as assistive prostheses, orthoses, and powered exoskeletons. A variable transmission is configured to automatically or manually adapt the torque profile to the demand of different locomotion tasks, such as a relatively high torque and low speed profile for a task such as standing up or ascending stairs, or a relatively low torque and high speed profile for a task such as walking.

20 Claims, 25 Drawing Sheets

(51) Int. Cl.
  *A61B 5/11*   (2006.01)
  *A61F 2/62*   (2006.01)
  *A61F 2/70*   (2006.01)
  *A61F 5/01*   (2006.01)
  *A61H 1/02*   (2006.01)
  *B25J 9/00*   (2006.01)
  *A61F 2/50*   (2006.01)
  *A61F 2/76*   (2006.01)

(52) U.S. Cl.
  CPC .............. *A61F 2/70* (2013.01); *A61F 5/0125* (2013.01); *A61H 1/024* (2013.01); *B25J 9/0006* (2013.01); *A61B 2562/0219* (2013.01); *A61F 2002/5003* (2013.01); *A61F 2002/5006* (2013.01); *A61F 2002/5007* (2013.01); *A61F 2002/502* (2013.01); *A61F 2002/5021* (2013.01); *A61F 2002/503* (2013.01); *A61F 2002/5038* (2013.01); *A61F 2002/701* (2013.01); *A61F 2002/704* (2013.01); *A61F 2002/7645* (2013.01); *A61F 2005/0137* (2013.01); *A61F 2005/0148* (2013.01); *A61F 2005/0155* (2013.01); *A61F 2005/0169* (2013.01); *A61F 2005/0179* (2013.01)

(56) References Cited

U.S. PATENT DOCUMENTS

| | | |
|---|---|---|
| 4,772,928 A | 9/1988 | Dietrich et al. |
| 5,027,657 A | 7/1991 | Juckenack et al. |
| 5,998,742 A | 12/1999 | Liu et al. |
| 6,166,013 A | 12/2000 | Coghlan et al. |
| 6,237,399 B1 | 5/2001 | Shivaram et al. |
| 6,829,510 B2 | 12/2004 | Nathan et al. |
| 7,279,010 B2 | 10/2007 | Cheng |
| 7,347,954 B2 | 3/2008 | Banno et al. |
| 7,437,954 B2 | 10/2008 | Sakano |
| 7,485,152 B2 | 2/2009 | Haynes et al. |
| 8,087,498 B2 | 1/2012 | Dupuis et al. |
| 8,500,823 B2 | 8/2013 | Herr et al. |
| 8,696,764 B2 | 4/2014 | Hansen et al. |
| 8,870,967 B2 | 10/2014 | Herr et al. |
| 8,974,543 B2 | 3/2015 | Balboni et al. |
| 9,089,443 B2 | 7/2015 | Nakaya et al. |
| 9,101,451 B2 | 8/2015 | Chugunov |
| 9,717,606 B2 | 8/2017 | Gramnaes |
| 9,770,347 B2 | 9/2017 | Shen |
| 9,808,357 B2 | 11/2017 | Langlois |
| 10,335,291 B2 | 7/2019 | Djian et al. |
| 10,342,681 B2 | 7/2019 | Herr et al. |
| 2002/0147336 A1 | 10/2002 | Liu et al. |
| 2003/0104365 A1 | 6/2003 | Gurney et al. |
| 2004/0121407 A1 | 6/2004 | Distefano et al. |
| 2005/0080061 A1 | 4/2005 | Belanoff |
| 2009/0088425 A1 | 4/2009 | Bailly et al. |
| 2009/0229378 A1 | 9/2009 | Kurtz et al. |
| 2010/0169988 A1 | 7/2010 | Kohli et al. |
| 2012/0028358 A1 | 2/2012 | Solodushko et al. |
| 2014/0276261 A1 | 9/2014 | Caires et al. |
| 2016/0041149 A1 | 2/2016 | Lindquist et al. |
| 2016/0158029 A1* | 6/2016 | Kuiken ............ A61F 2/64 623/24 |
| 2016/0242936 A1 | 8/2016 | Goldfarb et al. |
| 2016/0296346 A1 | 10/2016 | Burke et al. |
| 2017/0128312 A1 | 5/2017 | Park et al. |
| 2018/0116828 A1 | 5/2018 | Quinn et al. |
| 2018/0147073 A1 | 5/2018 | Ly et al. |
| 2018/0194000 A1 | 7/2018 | Smith et al. |
| 2018/0256372 A1 | 9/2018 | Boiten et al. |
| 2018/0325766 A1 | 11/2018 | Arzanpour et al. |
| 2018/0327373 A1 | 11/2018 | Yang et al. |
| 2019/0020934 A1 | 1/2019 | Goyal et al. |
| 2019/0160653 A1 | 5/2019 | Lee et al. |
| 2019/0209348 A1 | 7/2019 | Casler et al. |
| 2020/0038279 A1 | 2/2020 | Saccares et al. |

FOREIGN PATENT DOCUMENTS

| | | | |
|---|---|---|---|
| CN | 103271783 A | 9/2013 | |
| CN | 108836583 A | 11/2018 | |
| CN | 109044742 A | 12/2018 | |
| CN | 209695751 U | 11/2019 | |
| CN | 111110520 A | 5/2020 | |
| EP | 1933775 A2 | 6/2008 | |
| EP | 2178680 A2 | 4/2010 | |
| GB | 2302949 A | 2/1997 | |
| WO | 2007/027668 A2 | 3/2007 | |
| WO | 2009/016478 A2 | 2/2009 | |
| WO | WO 2009/015751 A1 * | 2/2009 | ............... A61F 2/58 |
| WO | 2016/094413 A1 | 6/2016 | |
| WO | 2018/087997 A1 | 5/2018 | |

OTHER PUBLICATIONS

Beil, Jonas, and Tamim Asfour. "New mechanism for a 3 DOF exoskeleton hip joint with five revolute and two prismatic joints." 2016 6th IEEE International Conference on Biomedical Robotics and Biomechatronics (BioRob). IEEE, 2016.

Beil, Jonas, Charlotte Marquardt, and Tamim Asfour. "Self-aligning exoskeleton hip joint: kinematic design with five revolute, three prismatic and one ball joint." 2017 International Conference on Rehabilitation Robotics (ICORR). IEEE, 2017.

International Search Report and Written Opinion received for PCT Patent Application No. PCT/US19/47536, mailed on Nov. 20, 2019, 8 pages.

International Search Report and Written Opinion received for PCT Patent Application No. PCT/US19/48489, mailed on Nov. 14, 2019, 8 ages.

International Search Report and Written Opinion received for PCT Patent Application No. PCT/US2020/000009, mailed on Feb. 9, 2021, 16 pages.

Leisle et al., "Cellular encoding of Cy dyes for single-molecule imaging", Elite vol. 5, 2016, pp. e19088.

Liu et al., "Imaging Live-Cell Dynamics and Structure at the Single-Molecule Level", Mol. Cell., vol. 58 No. 4, 2015, pp. 644-659.

Peng et al., "Site-specific bioorthogonal labeling for fluorescence imaging of intracellular proteins in living cells", J. Am. Chem. Soc., vol. 138, No. 43, 216, pp. 14423-14433, 2016.

Syed et al., "Expanding the Zebrafish Genetic Code through Site-Specific Introduction of Azido lysine", Bicyclononyne-lysine, and Diazirine-lysine. Int. J. Mol. Sci., vol. 20, No. 10, May 2019, pp. 2577.

Written Opinion received for PCT Patent Application No. PCT/US2020/000009, mailed on Jul. 22, 2020, 6 pages.

Lenzi Tommaso et al: "Actively variable transmission for robotic knee prostheses",2017 IEEE International Conference on Robotics and Automation (ICRA), IEEE, May 29, 2017 (May 29, 2017), pp. 6665-6671, XP033127567, DOI: 10.1109/ICRA.2017.7989787.

* cited by examiner

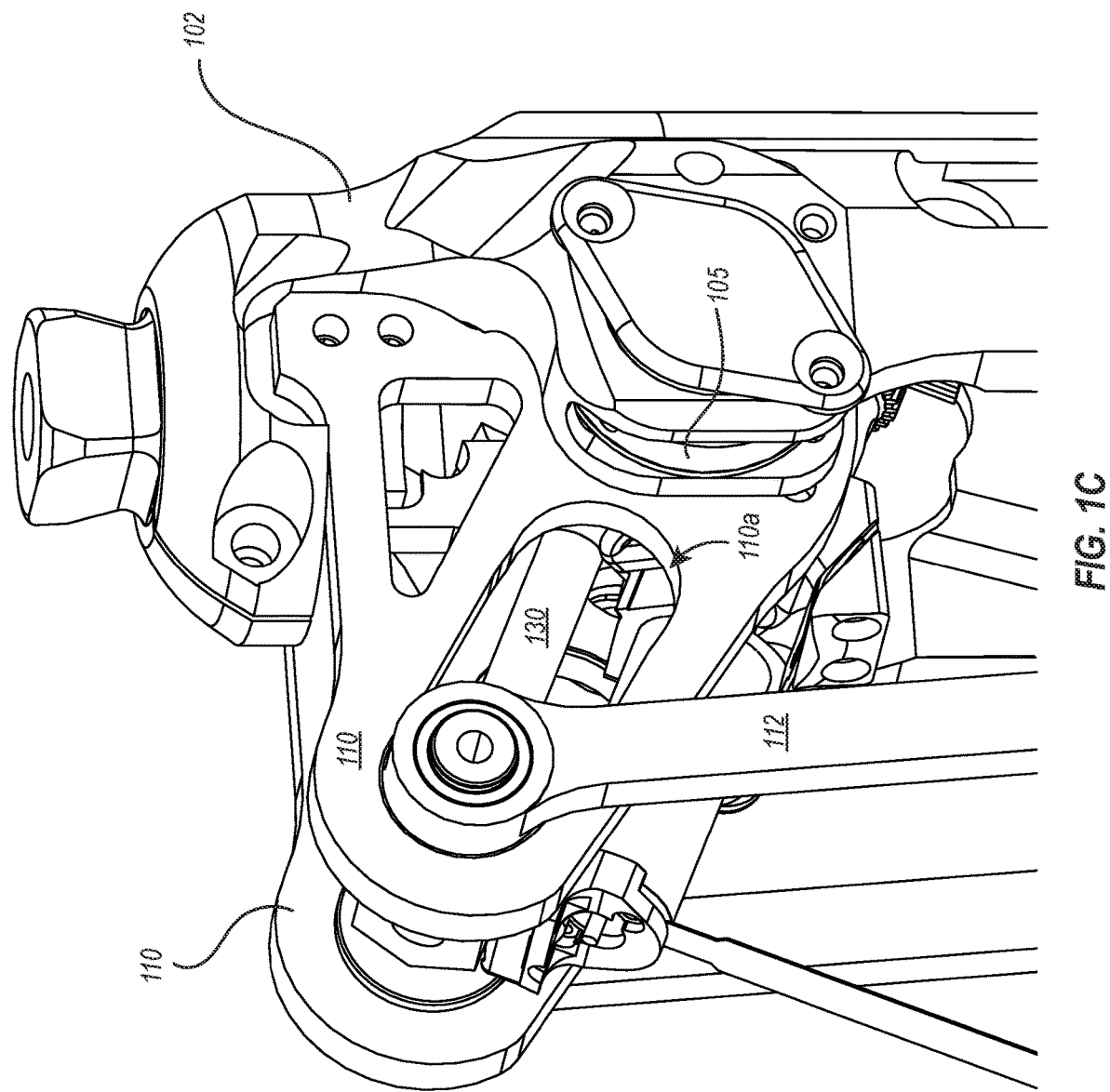

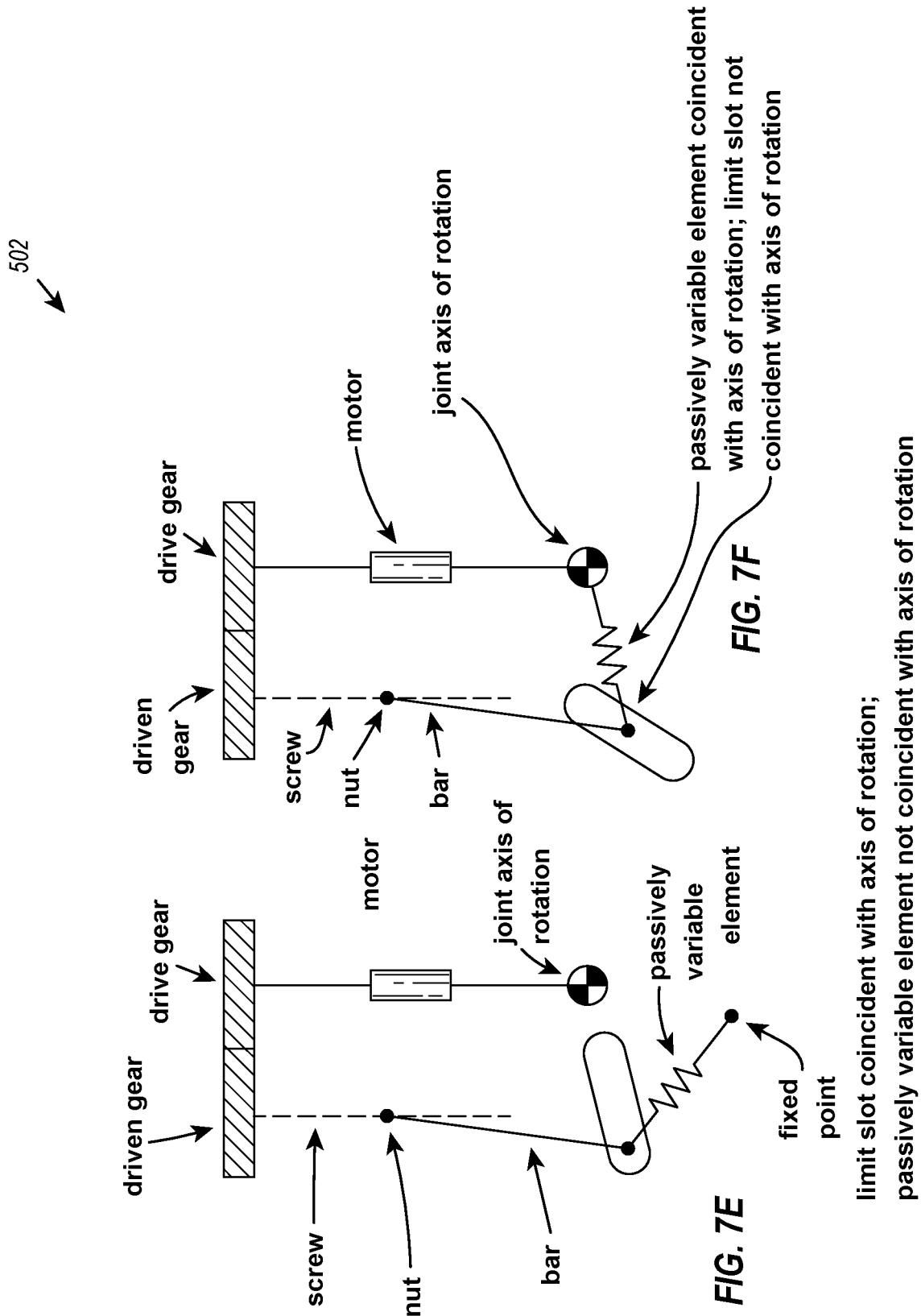

VARIABLE TRANSMISSION FOR ASSISTIVE PROSTHESIS DEVICE

CROSS-REFERENCE TO RELATED APPLICATIONS

This application claims priority to and the benefit of U.S. Provisional Patent Application No. 62/723,810, filed on Aug. 28, 2018 and titled "Actively Variable Transmission for Powered Assistive Devices and Related Methods," and to U.S. Provisional Patent Application No. 62/723,818, filed on Aug. 28, 2018 and titled "Passively Variable Transmission for Powered Assistive Prosthesis and Related Methods," the entireties of each of which are incorporated herein by this reference.

BACKGROUND

There are various assistive devices that may help to improve the mobility and functionality of some aspect of the anatomy of a user, including prosthesis devices, orthosis devices, and exoskeleton devices. Some of these assistive devices employ a transmission system of some type to facilitate their operation.

Typically, such transmission systems are configured to define, and operate in connection with, a fixed transmission ratio profile. As such, these transmission systems are, at best, optimized for only subset of possible locomotion tasks. Consequently, typical transmission systems are not well suited for use with locomotion tasks outside of the subset and, in fact, may be highly inefficient, or even unusable, when used with other locomotion tasks.

For example, an assistive device that is optimized for stair climbing may have a very high transmission ratio. As such, while the device may be well suited for stair climbing, the transmission components cannot operate fast enough to provide assistance in a locomotion task such as walking. On the other hand, an assistive device that is optimized for walking will have a lower transmission ratio, but the transmission components optimized for walking would likely perform poorly if an attempt were made to use that device for a stair ascent or comparable locomotion task. For example, if a motor is utilized to power the assistive device, the motor could overload and, for example, result in thermal limits being exceeded causing melting of the windings of the motor.

Accordingly, there is a long felt and ongoing need for assistive devices, such as prostheses, that include a transmission system capable of versatile use in performing a variety of locomotion tasks.

BRIEF SUMMARY

At least some embodiments of the present disclosure concern an assistive device having a transmission system that may automatically and/or manually adapt the torque and speed at an artificial joint, such as an artificial knee joint for example, to the demand of different locomotion tasks. For example, the transmission ratio of the variable transmission knee may be relatively high for locomotion tasks that require relatively high torque and relatively low speed, such as standing up from a seated position, stair climbing, or stair descending. Correspondingly, the transmission ratio of the variable transmission knee may be relatively low for tasks that require relatively high speed and relatively low torque, such as extending the knee to swing the leg forward during walking.

One example embodiment has been implemented in a powered knee prosthesis. The main actuation system of the prosthesis comprises a main motor (i.e., actuation motor) whose rotation is turned into translational motion (e.g., of a nut along a lead screw). The translational movement, through a slider-crank mechanism, rotates the knee joint to assist in implementation of the locomotion task. As used herein, the transmission ratio of the device is defined as the ratio between the motor speed and the knee joint speed, and may also be defined as the ratio between joint torque and motor torque. This transmission ratio may be significantly affected by the length of the crank, which can be actively changed with the disclosed variable transmission mechanism.

Advantageously, embodiments of the invention, including the mechanisms disclosed herein, can be used in powered assistive devices to increase the overall electrical efficiency of the devices, increase the mechanical efficiency of the devices, and/or to reduce the overall weight of the device. Embodiments of the invention may also enable users to successfully perform more subsets of ambulation tasks with device assistance and potentially reduce their physical and mental effort. Embodiments of the invention can be used in a variety of applications including, for example, powered prostheses, orthoses, exoskeletons, and robotic joints. As well, embodiments of the invention may be well suited for providing power assisted walking, in addition to other locomotion tasks such as climbing and descending stairs, and ascending/descending inclined surfaces such as ramps.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

A more particular description will be rendered by the embodiments illustrated in the appended drawings. It is appreciated that these drawings depict only exemplary embodiments of the disclosure and are therefore not to be considered limiting of its scope. In the accompanying drawings:

FIGS. 1A through 1C illustrate an exemplary assistive device having an actively variable transmission system/mechanism;

FIGS. 7A through 7I illustrate additional embodiments of passively variable transmission systems/mechanisms that may be integrated with an assistive device;

DETAILED DESCRIPTION

Introduction and Definitions

Figure 1A:
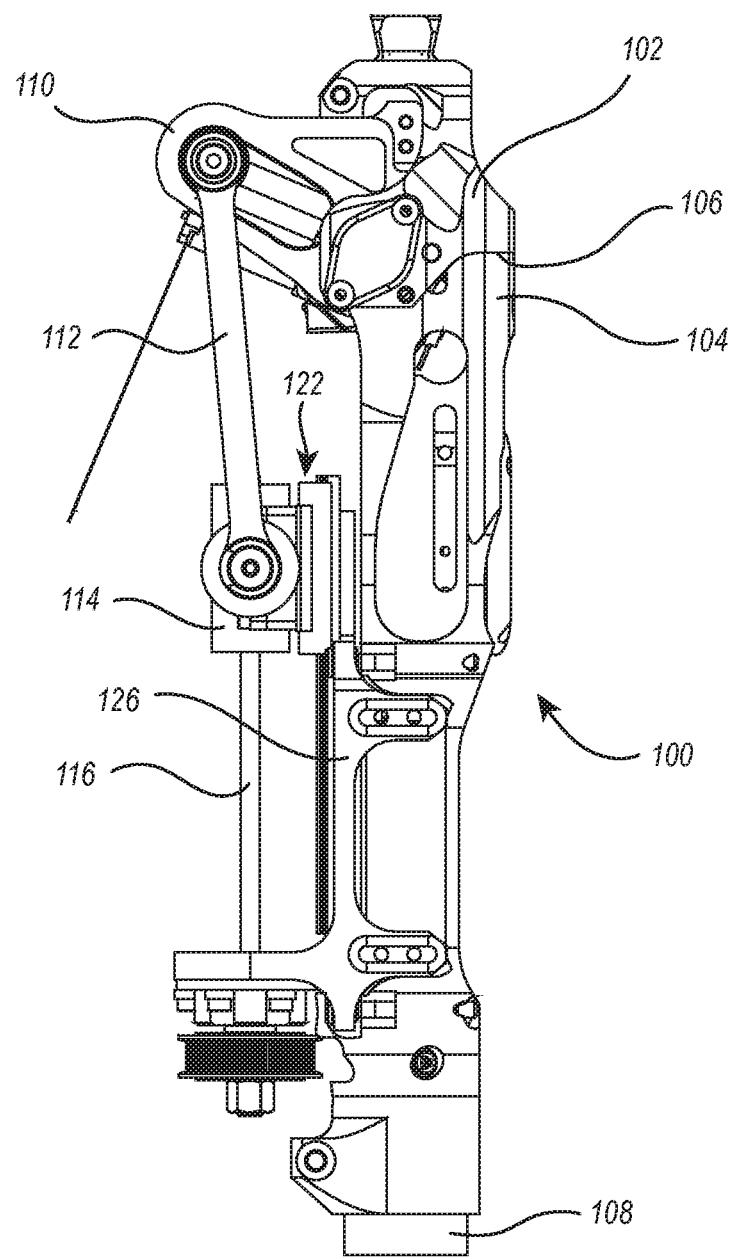

As noted above, some example embodiments disclosed herein are described in connection with the structure and function of a human knee joint. However, the scope of the invention is not so limited and extends, more generally, to assistive prostheses, orthoses, and exoskeletons (collectively referred to herein as "assistive device(s)") for any other joints that could benefit from variations in a transmission ratio depending upon the task performed in whole or in part by that joint.

Embodiments described herein may be well suited for providing power assisted walking, in addition to other locomotion tasks such as climbing and descending stairs, and ascending/descending inclined surfaces such as ramps. While reference is made herein to such "locomotion tasks," the scope of the invention is not limited to these specific locomotion tasks. Rather, this disclosure extends more broadly to any other human and/or animal task that may be performed by and/or assisted by an assistive prosthesis, examples of which are disclosed herein.

Torque and speed requirements may vary from one locomotion task to another. For example, stair climbing may require high torque/low speed operation of the joint, while walking may require low torque/high speed operation of the joint. As well, the torque/speed requirements may vary within a particular locomotion task. For example, extension of the artificial joint during stair climbing, where the knee must extend starting from angles that may be on the order of 50-80 degrees, may require a relatively high torque/low speed input, as this is the portion of the ascension gait sequence that essentially lifts the body weight of the user.

This disclosure includes various embodiments specific to human lower limb applications, however, the scope of the invention is not so limited. Thus, for example, other embodiments enabled by this disclosure include, but are not limited to, upper limb applications and robotic joints usable in, for example, a humanoid robot, legged robot, or other application.

In general, embodiments of the invention may include an actuation mechanism that is operable to rotate an artificial joint, such as a knee joint for example. The actuation mechanism may include a motor for motorized operation of the artificial joint. The actuation mechanism may be operable independently of, and/or in conjunction with, non-assisted operation (i.e., manually-powered operation) of the artificial joint by a user.

Embodiments may be constructed of any suitable material(s). Structural elements and/or other elements may be constructed of metals, such as aluminum, titanium, or steel, as well as composites, carbon, carbon fiber materials, and any other materials that are relatively light and offer relatively good strength and durability. A variety of plastics may be used as well for one or more elements of embodiments of the invention.

Where two or more elements of an embodiment are rotatably connected to each other, any suitable mechanisms and elements may be employed to implement the rotatable connection. For example, pins, solid or hollow shafts, bolts, and rivets, may comprise an element of a rotatable connection. Likewise, ancillary components such as bushings, sleeves, and bearings of any suitable type, may be provided as part of one or more of the disclosed rotatable connections.

Moreover, the speed ratio and/or the torque ratio can be changed during operation of the disclosed embodiments. For example, when a disclosed knee joint is undergoing flexion, or extension, the speed ratio and/or torque ratio of the knee joint can be modified while the associated task is being performed.

Some embodiments described herein include an "actively variable transmission system," while other embodiments include a "passively variable transmission system," each of which are described in more detail below. Although described separately for the purpose of more focused disclosure, it will be understood that some embodiments of assistive devices may include a combination of both one or more actively variable transmission system and one or more passively variable transmission system. For example, an assistive device having multiple artificial joints may integrate one or more joints with an actively variable transmission system and one or more joint with a passively variable transmission system.

It should be noted that due to the deformable nature of compliant elements, such as the passively variable elements disclosed herein, the ratio of the speed and the inverse ratio of the torque are not necessarily equal to each other, and are not equal in some embodiments. This may occur, for example, in systems that experience a dynamic lag between an input, such as motor speed, and an output, such as torque at the joint. In this example, the dynamic lag, which is sometimes also referred to as rate-dependent hysteresis, is caused by the deformability of the passively variable element. In some systems that experience dynamic lag, it may be possible to reduce, or eliminate, the dynamic lag if the input is varied relatively slowly. However, it may not always be desirable to vary the input slowly. As should be apparent, systems that experience dynamic lag are non-linear in nature.

As well, passively variable elements can be configured to provide linear and/or non-linear responses to an input from a user and/or from a motor. More specifically, various embodiments can implement non-linear, or variable, stiffness and/or damping in response to an input. As such, the scope of the invention embraces both linear and non-linear systems.

In addition to the main actuation system, embodiments of the invention may also include one or more passively variable elements configured to deform in some way, such as by changing length and/or orientation for example, based on the direction and magnitude of the torques and forces input by the motor of the main actuation system and/or input by the user. The deformation of the passively variable element(s), such as a change in length, consequently alters the speed and torque ratios of the assistive prosthesis based on the configuration of the device.

As used herein, and discussed in more detail elsewhere in this disclosure, a passively variable element is a physical element, or group of physical elements, that physically deforms, or otherwise changes physical configuration, in response to an input by one or more power sources connected to the passively variable element. Such passively variable elements may be referred to as being 'compliant' in nature. The passively variable element can return automatically to an undeformed, relatively less deformed, or different physical, state upon reduction or cessation of the power source input. To illustrate, a spring may return on its own to an undeformed, or relatively less deformed, state when a deforming force previously applied to that spring is reduced, or removed. As well, a passively variable element may be deformed, or have its physical configuration otherwise temporarily modified, in response to application of power and/or forces to the passively variable element. By way of contrast, an element that is not passively variable may simply change its position or location in response to application of power and/or a force, but will not change is physical configuration in any substantial way.

The passively variable element(s) can exhibit various types of behavior. For example, a passively variable element may be configured in the form of a spring that is able to elastically deform, at least over a certain range of deformations. As another example, a passively variable element may take the form of a damper for example, that exhibits viscous behavior. In other instances, a single passively variable element, or a group of passively variable elements, may exhibit both elastic and viscous behaviors. Regardless of the physical configuration or arrangement of the passively variable element(s), the elastic behavior of a passively variable element may be linear, that is, the ratio of the change in forces/torques on the passively variable element over the range of the physical deformation of the passively variable element may be constant, in the case of elastic behavior. Somewhat similarly, the viscous behavior of a passively variable element may also be linear, that is, the ratio of the change in forces/torques on the passively variable element is constant for a given velocity of the element that is connected to, and causes the deformation of, the passively variable element.

Additionally, or alternatively, the elastic and/or viscous behaviors of a passively variable element may be nonlinear. That is, the ratio of the change in forces/torques on the passively variable element over the range of the physical deformation of the passively variable element may not be constant.

In addition, the stiffness and damping coefficients of a passively variable element may be constant or variable. Such passively variable elements may thus be referred to, in the latter case, as having a variable stiffness and variable damping. In more detail, as the configuration of the passively variable element changes, the path of translation/rotation of one end of the passively variable element with respect to its other end may be linear, that is, along/around one axis, or nonlinear/curved, that is, along/around more than one axis. If more than one passively variable element is used, the passively variable elements may be connected in series or in parallel.

As well, different types of passively variable elements may be combined in a single assistive device. To illustrate, an assistive prosthesis may include one or more passively variable elements that exhibit elastic behavior and the same assistive prosthesis may also include one or more passively variable elements that exhibit viscous behavior.

With regard to passively variable elements, those may be made of any suitable materials. Where a passively variable element comprises, or consists of, one or more springs, which can be arranged in series or in parallel, the springs may be made of any suitable material(s), examples of which include metal, plastic, and rubber, or combinations of any of these. As used herein, the term 'spring' is intended to be broadly construed and, as such, embraces any structure or combination of structures whose behavior, at least in an elastic range, can be characterized by an equation of the form: $F=Kx$ (Hooke's Law), where $F$=applied force, $K$=spring constant, and $x$=displacement. Other example springs include elements configured as an endless loop, or belt. However, the scope of the invention is not limited to any particular type or configuration of spring.

Where a passively variable element comprises, or consists of, one or more dampers such as viscous dampers, which can be arranged in series or in parallel, the dampers may comprise, or consist of, mechanisms such as a dash pot. More generally, the damper may comprise, or consist of, any mechanism that involves movement of one or more elements through a fluid, or combination of fluids, in response to a power input or multiple power inputs. As used herein, the term 'damper' is intended to be broadly construed and, as such, embraces any structure or combination of structures whose behavior can be characterized by an equation of the form: $F=-Cv$, where $F$=applied force, $c$=damping constant of proportionality, and $v$=velocity. Example dampers may be configured as a hydraulic shock, or gas shock. However, the scope of the invention is not limited to any particular type or configuration of damper.

With respect to walking, the crank (discussed elsewhere herein) does not have to collapse to the knee joint and get disconnected from the main motor during walking mode. At least some embodiments of the invention may employ various sensors and microprocessors. The sensors may include accelerometers, as well as sensors that can detect the position of an object in three-dimensional space. Embodiments of the invention are configured to transition between locomotion modes, and to provide powered assistance to the user in one, some, or all, of the locomotion modes.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

It will be understood that elements described in relation to any embodiment depicted and/or described herein may be substituted for or combined with elements described in relation to any other embodiment depicted and/or described herein.

Example Actuation Mechanisms

Figure 1B:
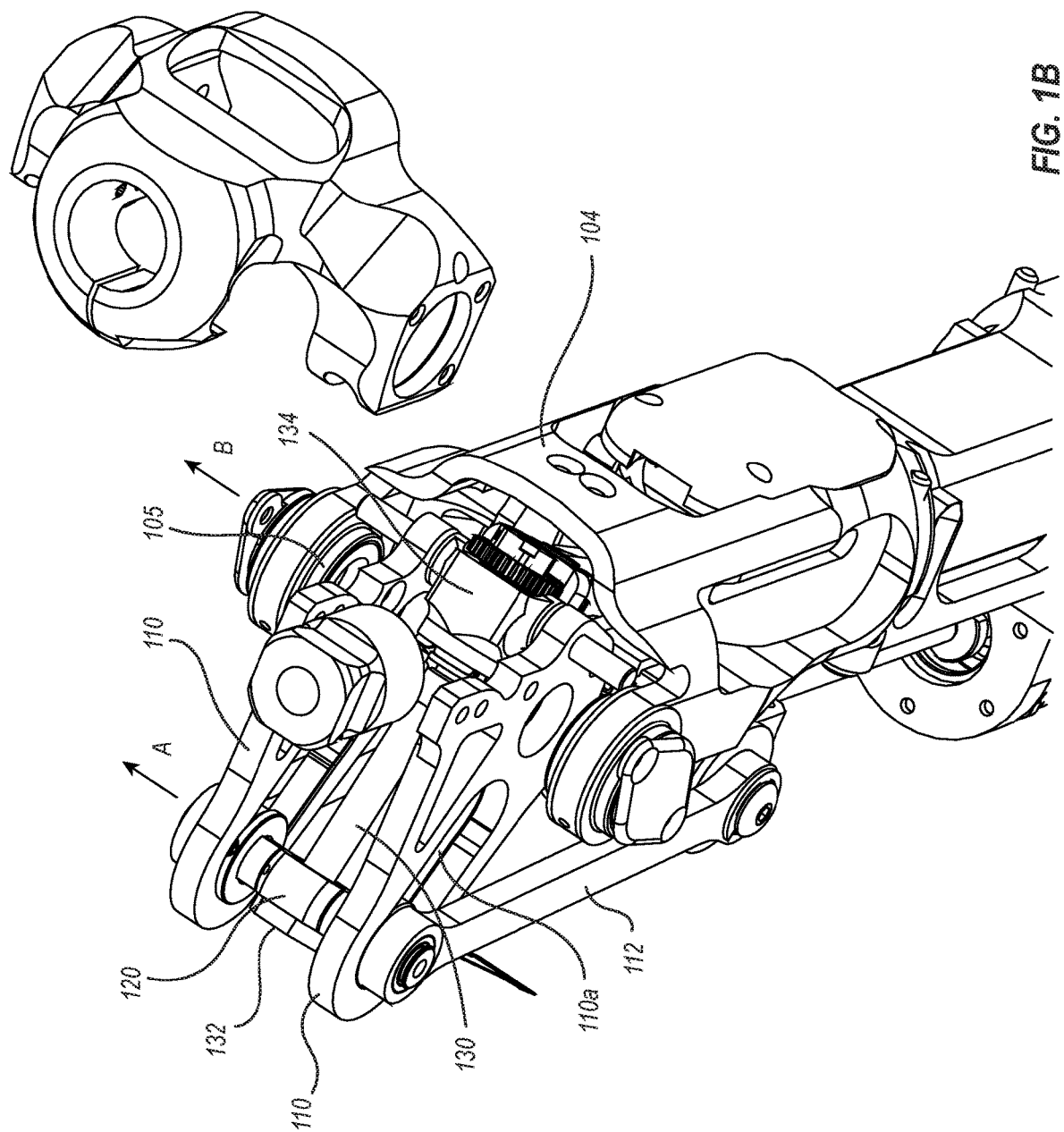

As shown in FIGS. 1A through 1C, an assistive device (here, an assistive prosthesis 100) may include a head portion 102 and foot portion 104 that are rotatably connected to each other by way of a one or more shafts 105. The head portion 102, foot portion 104, and shafts 105 collectively define a rotatable joint 106, such as a knee joint for example, which is able to bend at the line indicated by reference 106 so that the head portion 102 is able to rotate toward, and away from, the foot portion 104. In some embodiments, the range of rotation of the head portion 102 relative to the foot portion is about 90 degrees, but may be more, or less than, 90 degrees in other embodiments. In the example of FIGS. 1A through 1C, the head portion 102 has been fully rotated into contact with the foot portion 104. Where the rotatable joint 106 comprises a knee joint, the illustrated configuration illustrates a knee joint in an extended/unbent state.

With continued reference to FIGS. 1A through 1C, the upper or lower end of the device may include, or be connected to, a pylon 108 of a length suitable to meet the needs and anatomy of a particular user. Additionally, or alternatively, the upper or lower end of the device may include a pyramid adaptor or other suitable prosthesis componentry such as for use to releasably connect the assistive prosthesis 100 to another prosthetic element.

Operation, that is, rotation, of the rotatable joint 106 is effected by way of an actuation system that includes a pair of flanges 110, a pair of bars 112, a nut 114, and screw 116. In more detail, the flanges 110 are each fixed to the head portion 102 so that as the flanges 110 rotate, the rest of the head portion 102 also rotates, relative to the foot portion 104, in unison with the flanges 110.

As perhaps best shown in FIG. 1B, a pivot shaft 120 is provided that extends through a longitudinal cutout section 110a defined by the flanges 110. Thus, as the pivot shaft 120 is pushed up, or pulled down against the flanges 110, the flanges 110 act to rotate the head portion 102, relative to the foot portion 104, about the shafts 105.

Movement of the pivot shaft 120 upward and downward is effected by way of the bars 112, each of which is rotatably connected to a respective end of the pivot shaft 120. That is, as the bars 112 move upward, the flange 110 and, thus, the head portion 102, are caused to rotate clockwise (with reference to the perspective of FIG. 1), causing joint extension. On the other hand, as the bars 112 move downward, the flanges 110 and, thus, the head portion 102, are caused to rotate counterclockwise (with reference to the perspective of FIG. 1), causing joint flexion.

As noted earlier, the actuation mechanism includes a nut 114, to which the respective lower ends of the bars 112 are rotatably connected. The nut 114, in turn, may be internally threaded so as to be movable lengthwise along the correspondingly threaded screw 116. The nut 114 may also be connected to a slider 122 configured for translational movement along a track. The track may not extend the full length of the screw 116 and, instead, may be positioned near only the upper portion of the screw 116. Among other things the slider 122 and track may function to provide stability to the nut 114 as it moves along the screw 116. The track may, in tam, be connected to a foot flange 126 that is connected to the foot portion 104.

Because the position of the screw 116 is fixed, rotation of the screw 116, such as by an actuation motor (not shown—may optionally be positioned within the lower end of the foot portion 104), causes the nut 114 to move up and down along the screw 116. As the nut 114 is indirectly connected to the pivot shaft 120 by way of the bars 112, movement of the nut 114 causes a corresponding upward or downward movement of the flanges 110 under the influence of the pivot shaft 120 and, thus, rotation of the head portion 102 relative to the foot portion 104.

With respect to the aforementioned motor, a pulley (and/or sprocket or other suitable power transmission structure(s)) may be connected to the screw 116 so that rotation of the pulley, which may be connected to the actuation motor (not shown) by way of a belt (not shown), causes a corresponding rotation of the screw 116. Thus, the motor may be a reversible type that can be controlled to rotate in two opposite directions to rotate the screw 116 and thereby move the nut 114 up or down along the screw 116. The motor may be controlled automatically, such as by way of sensors, and/or maybe controlled manually/ad hoc by a user with a user console (not shown) or comparable control device.

Actively Variable Transmission Systems

In general, embodiments may include an active transmission mechanism that is operable to adjust the configuration of an artificial joint, such as a knee joint for example, to suit the torque and speed requirements associated with performance of a particular locomotion task involving the artificial joint, examples of which include stair climbing/descending, walking, and inclined surface ascending/descending. The transmission mechanism may include a motor (referred to herein as "transmission motor" to distinguish from the actuation motor) for motorized adjustment of the configuration of the artificial joint. The transmission mechanism may be operable independently of, and/or in conjunction with, the operation of an actuation mechanism. Further details concerning an example transmission mechanism are provided in the following discussion.

As noted above, embodiments of the invention may include a pivot shaft 120 to which a pair of bars 112 are rotatably connected. The pivot shaft 120 extends through respective longitudinal cutout sections 110a defined by each of a pair of flanges 110. As apparent from FIG. 1B, a position of a longitudinal axis A defined by the pivot shaft 120 is adjustable relative to a longitudinal axis B corresponding to the axis of rotation of the head portion 102 relative to the foot portion 104.

It should be noted that the distance between the longitudinal axes A and B may be referred to herein as a moment arm or, alternatively, as a crank length. As such, the moment arm is at a maximum when the pivot shaft 120 is positioned as shown in FIGS. 1A through 1C, and the moment arm is at a minimum when the pivot shaft 120 is positioned at the opposite end of the longitudinal cutout sections 110a.

Correspondingly then, when the longitudinal axis A defined by the pivot shaft 120 is at a maximum distance from a longitudinal axis B, the torque at the artificial joint 106 is at a relative maximum, and the speed of rotation of the head portion 102, relative to a given actuation motor speed, may be at a relative minimum. The combination of a torque value with a corresponding speed value may be referred to as a transmission ratio profile. Conversely, when the longitudinal axis A defined by the pivot shaft 120 is at a minimum distance from a longitudinal axis B, the torque at the artificial joint 106 is at a relative minimum, and the speed of rotation of the head portion 102, relative to a given actuation motor speed, may be at a relative maximum. Intermediate positions of the pivot shaft 120 in the longitudinal cutout sections 110a correspond to respective intermediate values of torque and speed at the artificial joint 106. Thus, the transmission ratio profile may be at a maximum when the moment arm is at its maximum length, and the transmission ratio profile may be at a minimum when the moment arm is at its minimum length.

As will be appreciated from the foregoing discussion, it is useful to be able to change, and fix, the position of the pivot shaft 120 at various different locations along the longitudinal cutout sections 110a, depending upon the locomotion task that is to be undertaken and, thus, the torque and speed requirements of a particular locomotion task. Each different position of the pivot shaft 120 may correspond to a respective combination of a torque profile and speed profile.

To that end, the example embodiment of a transmission mechanism includes a leadscrew 130 that may be externally threaded (not shown in the Figures). The leadscrew 130 may be connected to the pivot shaft 120 in any suitable manner. In some embodiments, the leadscrew 130 passes through a hole in the pivot shaft 120 and is connected to a nut 132 that serves to prevent withdrawal of the leadscrew 130 from the opening in the pivot shaft 120. The hole of the pivot shaft 120 that receives the leadscrew 130 may be threaded so that as the leadscrew 130 rotates, the pivot shaft 120 moves along the leadscrew 130. Alternatively, the hole of the pivot shaft 120 that receives the leadscrew 130 may be unthreaded, and the nut 132 may be fixed to the pivot shaft 120 and threadingly engage the leadscrew 130. In either example configuration, rotation of the leadscrew 130 effects a change in the position of the pivot shaft 120 and, thus, a change to the transmission profile of the transmission mechanism, as explained earlier.

Rotation of the leadscrew 130 and, accordingly, movement of the pivot shaft 120, may be effected by a transmission 134 to which a transmission motor (not shown) is coupled. Thus, this motor, similar to the motor of the actuation system, may be a reversible type that can be controlled to rotate in opposite directions to rotate the leadscrew 130 and thereby change the position of the pivot shaft 120 along the leadscrew 130 in order to achieve a particular transmission ratio profile. The transmission motor may be controlled automatically, such as by way of sensors, and/or may be controlled manually/ad hoc by a user with a user console (not shown) or comparable control device.

As well, adjustments to the position of the pivot shaft 120 along the longitudinal cutout sections 110a can be performed separately from, and/or in conjunction with, operation of the artificial joint 106 by movement of the flanges 110. As such, adjustments to a transmission ratio profile can be performed in parallel, or in series, with operation of the artificial joint 106.

Example Control Systems

Figure 2A:
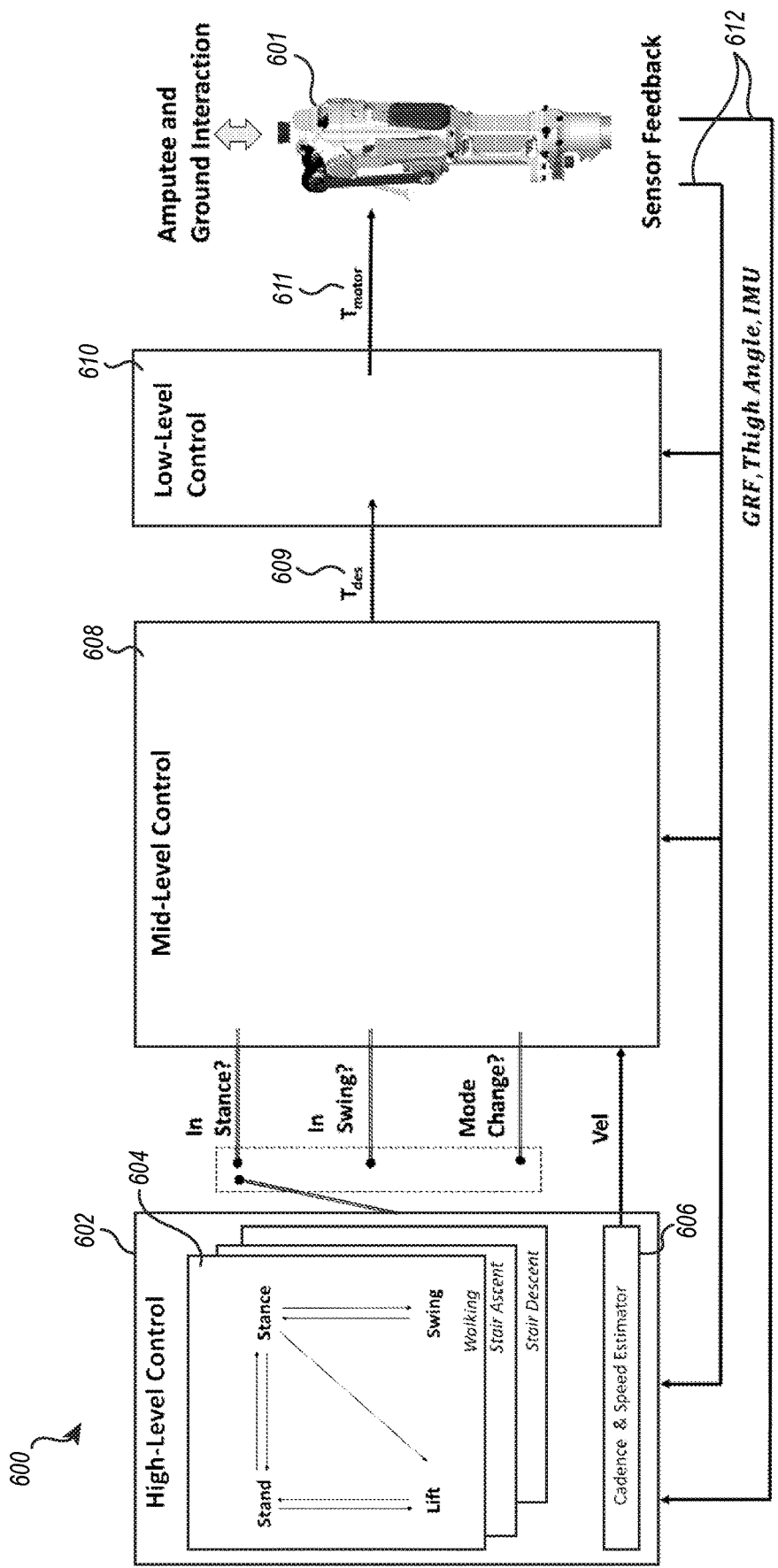
FIGS. 2A and 2B illustrate components of an exemplary control system that may be utilized to automatically control the actively variable transmission system/mechanism.

FIG. 2A schematically illustrates an example control system 600 operable to determine an ambulation mode and automatically adjust the actively variable transmission system accordingly. In the system, a high-level controller 602 includes a plurality of ambulation mode profiles 604, including, in this example, walking, stair ascent, and stair descent. Each ambulation mode profile 604 includes a set of movement states: Lift, Stand, Stance, and Swing. Each ambulation mode profile 604 may include its own particular finite-state machine, and each movement state may include its own particular control algorithm. These are sent to a mid-level controller 608. Using the state-specific algorithms, the mid-level controller 608 generates a desired joint torque 609 (Tdes), which is then sent to a low-level controller 610. The low-level controller 610 operates to translate the desired joint torque 609 into functional motor commands 611 (Tmotor) (e.g., current, voltage, and/or speed commands) for the actuation motor and/or transmission motor. The assistive device 601 (which may represent any of the other assistive devices described herein) then adjusts accordingly to an updated torque configuration.

Determination of movement state may be made on the basis of a thigh angle/orientation measurement and the ground reaction force (GRF), which may be measured using sensors associated with the assistive device 601 and relayed to the high-level controller 602 via feedback communication 612. GRF information may be used to indicate whether the assistive device 601 is lifted off or in contact with the ground. Thigh orientation is an indication of the posture of the user, which is utilized to signal the intent to take a step.

In one example embodiment, from the "Lift" state, the controller transitions to the "Stand" state upon measuring a GRF greater than a lift threshold, such as about 5% (e.g., about 3% to about 10%) of the user's body weight, and conversely transitions back to the "Lift" state upon measuring a GRF less than the lift threshold. From the "Stand" state, the controller transitions to the "Stance" state if the thigh orientation is less than an orientation threshold, which differs depending on ambulation mode profile 604. From the "Stance" state, the controller transitions to the "Swing" state if the GRF is less than the lift threshold, but back to the "Stand" state if the absolute value of the thigh orientation is lower than an orientation threshold for longer than a stance duration limit (e.g., about 100 to 500 ms, or about 200 ms).

The high-level controller 602 may also include a cadence and speed estimator 606, which may include a timer for use, optionally in combination with the other high-level controller 602 components, to estimate a gait cadence and/or speed. The outputs of the high-level controller 602, including the determined movement state and the cadence/speed estimate are transmitted to the low-level controller 610 to define desired joint behavior.

The mid-level controller 608 operates to generate the desired joint torque 609. Different algorithms may be utilized for different movement states. For example, in the "Stance" state, quasi-stiffness profiles extracted from nominal biomechanics may be utilized to generate desired joint torque 609 based on joint position and ambulation speed. In the "Swing" state, the desired joint torque 609 may be based, at least in part, on a minimum jerk profile, which may be adapted based on a final knee position, joint position and velocity at transition between "Stance" and "Swing," and/or based on estimated gait cadence/speed. The "Swing" state algorithm may also utilize different final knee position inputs based on the particular ambulation mode profile 604 (e.g., about 5° for walking, about 55° for stair ascent) and/or intermediate knee position inputs (e.g., about 65° for walking, about 90° for stair ascent). Desired knee position is then converted to a desired joint torque 609 based on feedback 612 and/or gravity/inertia compensation inputs.

The mid-level controller 608 may also operate to synchronize the actuation motor and the transmission motor during transitions between different ambulation modes. When a mode transition is triggered, two minimum jerk profiles may be generated to enable smooth operation of the motors to move to the desired configurations based on current positions and desired transition duration. In some embodiments, ambulation mode transition may be restricted to when the device is in one or more defined positions, such as when the joint is fully extended.

Figure 2B:
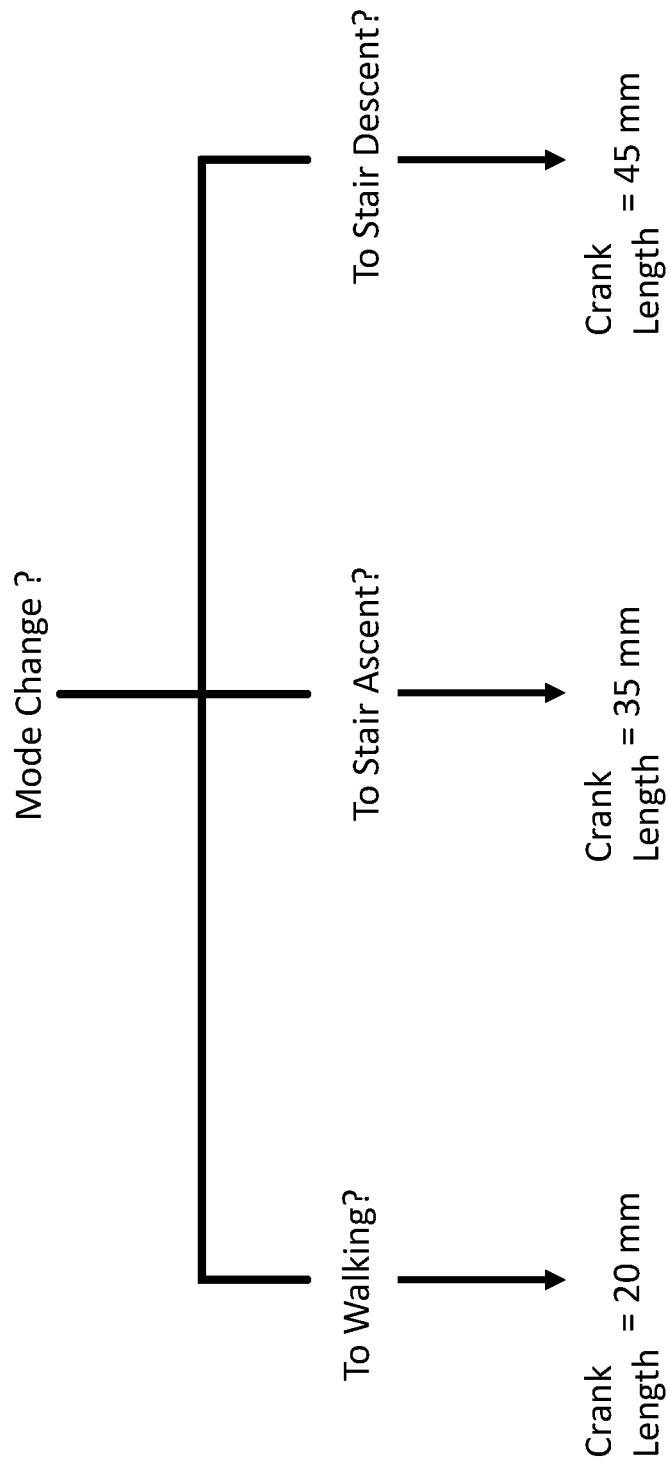

FIG. 2B illustrates an example of crank lengths (e.g., distance between axes A and B as shown in FIG. 1B) that can result from a determined ambulation mode. While these crank lengths are exemplary, it will be understood that other applications may utilize other crank lengths because of differences in particular user anatomy, user preferences, type of assistive device, type of joint, or other particular application needs. Nevertheless, an ascent modulation mode will typically have a longer crank length than a walking modulation mode (e.g., by about 1.2 to 3 times, or by about 1.5 to 2.5 times), while a descent modulation mode will typically have a still longer crank length (e.g., by about an additional 1.2 to 3 times, or by about 1.5 to 2.5 times).

Passively Variable Transmission Systems

Figure 3A:
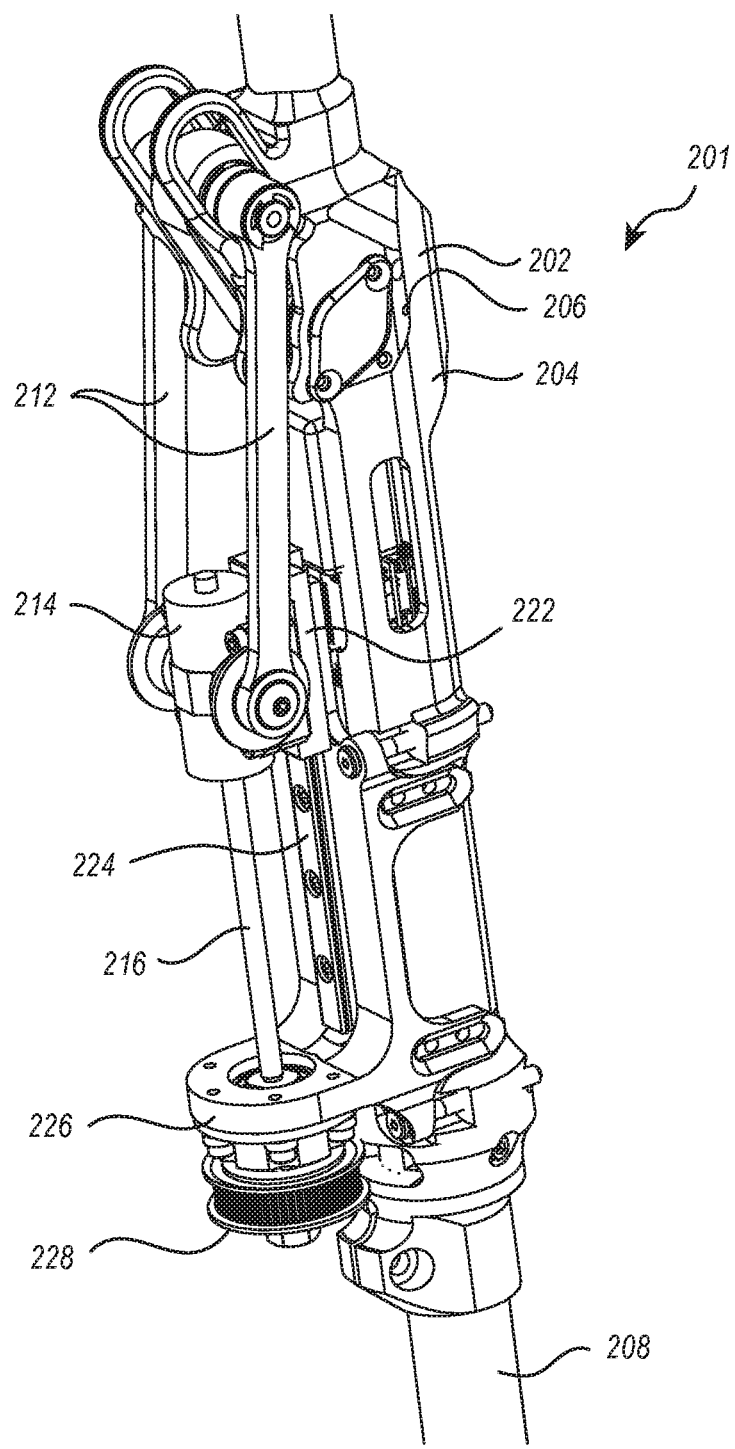
FIGS. 3A through 3C illustrate various perspective views of an exemplary assistive device having a passively variable transmission system/mechanism.
Figure 3B:
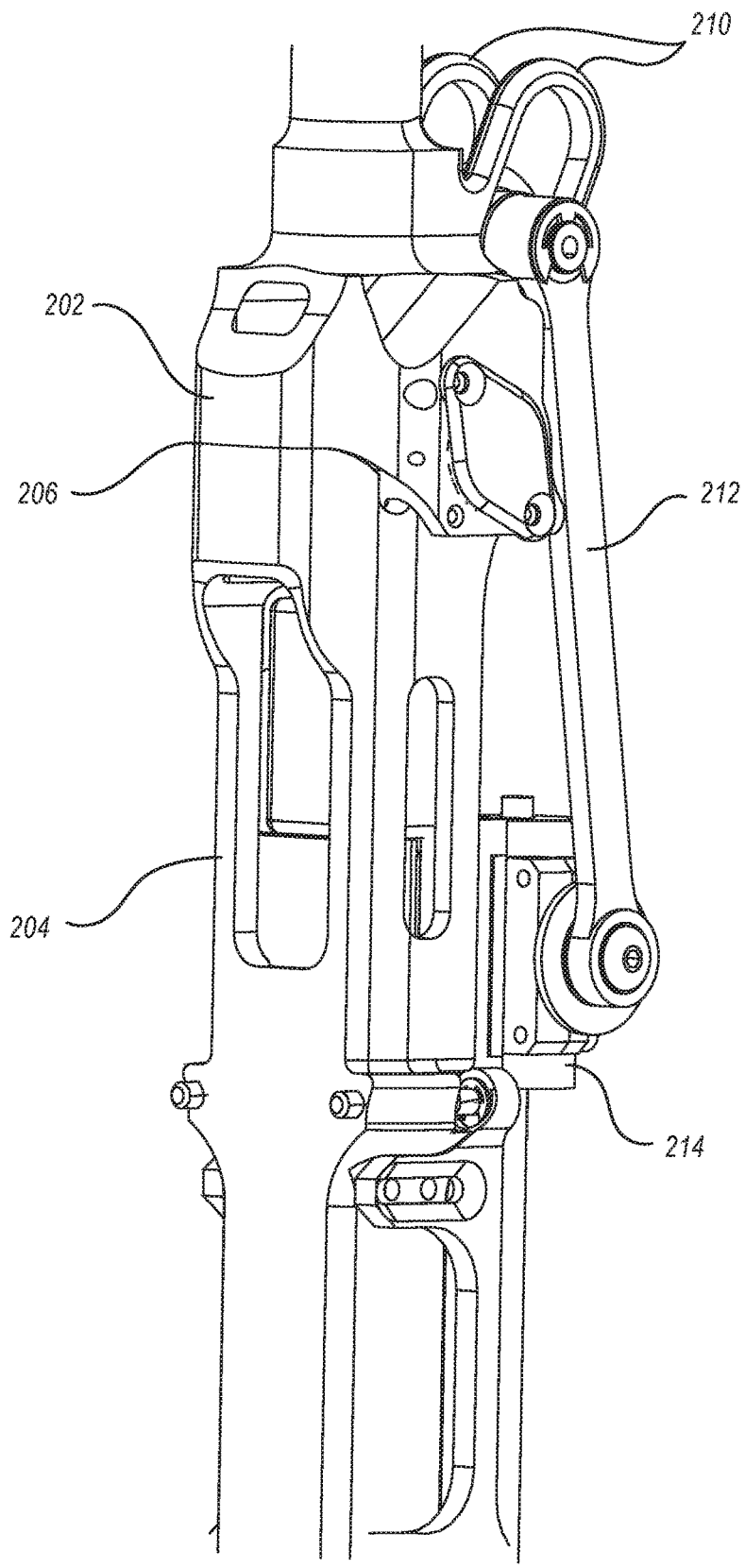
Figure 3C:
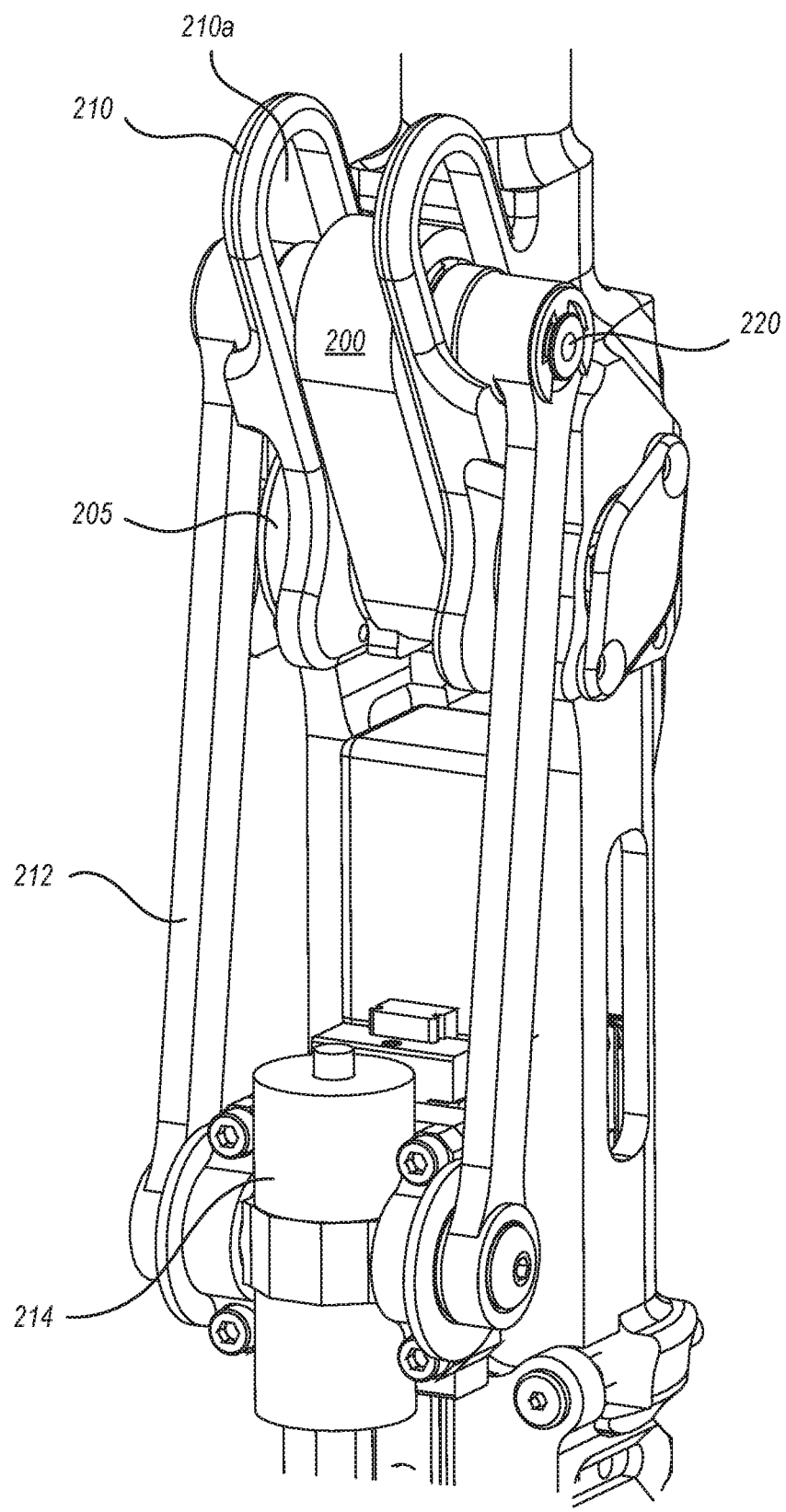

FIGS. 3A through 3C illustrate an embodiment of an assistive device 201 having a passively variable transmission system. The assistive device 201 may have an actuation system similar to the actuation system described above in relation to assistive device 100, with like numerals representing like components. Briefly, the assistive device 201 includes a head portion 202 and foot portion 204 rotatably connected to one another on one or more shafts 205 to define a rotatable joint 206. One or more pylons 208, pyramid adaptors (not shown), and/or other prosthesis componentry may be provided at the upper and/or lower end of the device.

The actuation system may include a pair of flanges 210 connected to the head portion 202, a pair of bars 212, a nut 214 (which may be internally threaded), and a screw 216. A pivot shaft 220 is connected to the bars 212 and extends through the cutout section 210a. The nut 214 may also be connected to a slider 222 that is slidable along track 224, which is connected to a foot flange 226. An actuation motor (not shown) may be mechanically coupled to pulley 218 (and/or other power transmission elements) to drive rotation of the screw 216 and thus translation of the nut 214, which in turn drives movement of the bars 212 and rotation of the head portion 202 relative to the foot portion 204.

As perhaps best shown in FIG. 3C, the assistive device 201 may include one or more passively variable elements 200. In general, a passively variable element of the transmission mechanism may be connected to one or multiple power sources, each of which can provide a respective torque input to the passively variable element which, in turn, will result in a change, such as an elastic deformation, in the configuration of the passively variable element. Additionally, or alternatively, a torque input to the passively variable element may change a position and/or orientation of the passively variable element.

Thus, for example, a passively variable element may deform in response to an input, allowing the torque configuration (i.e., the relative position of the pivot shaft 220 within the cutout section 210a) to dynamically adjust. Additionally, or alternatively, the potential energy stored in the passively variable element as a result of the input/deformation may subsequently be released/applied to assist in operation of the artificial joint.

Figure 4A:
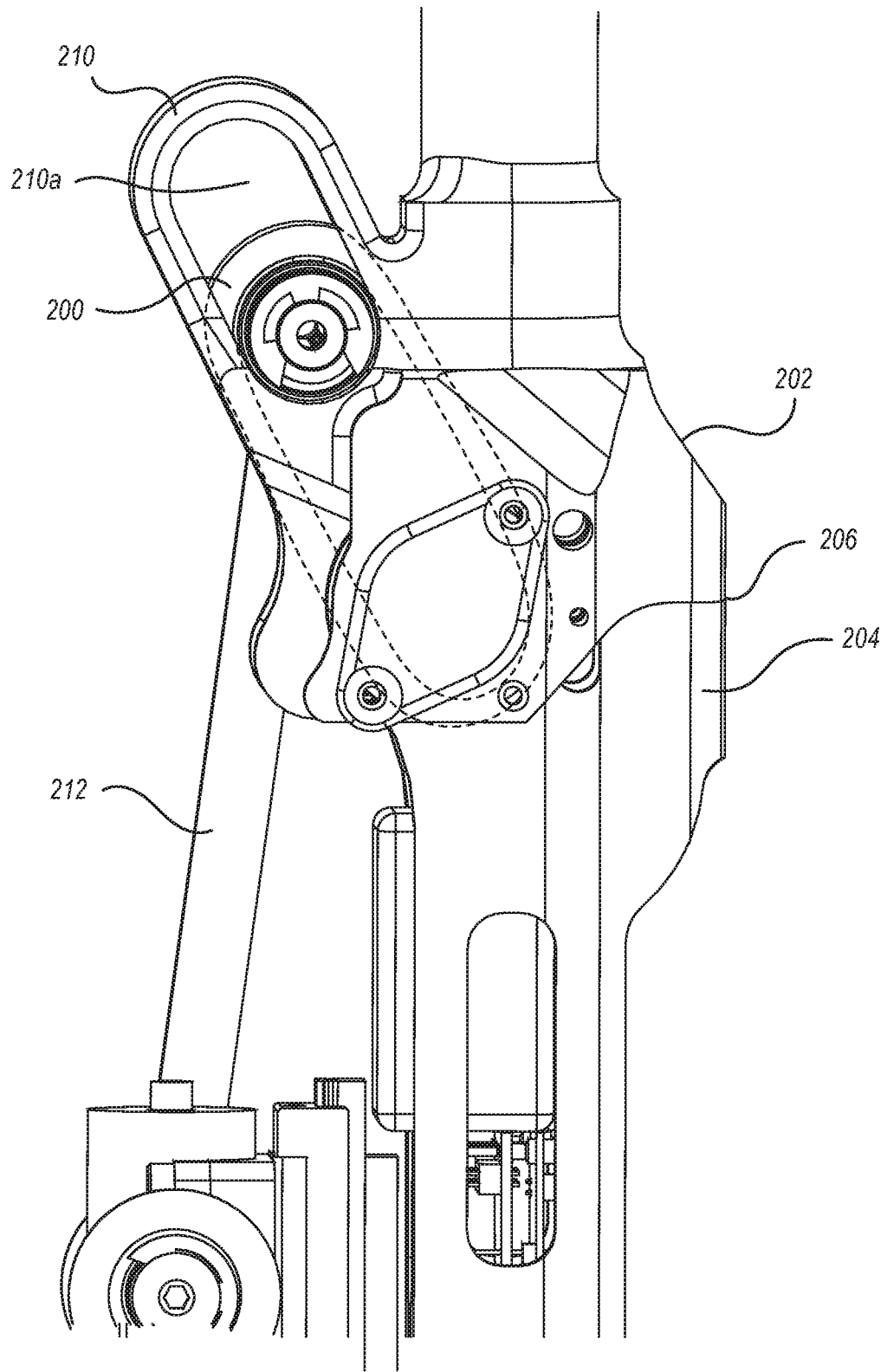
FIGS. 4A through 4C illustrate various views of another exemplary assistive device having a passively variable transmission system/mechanism.
Figure 4B:
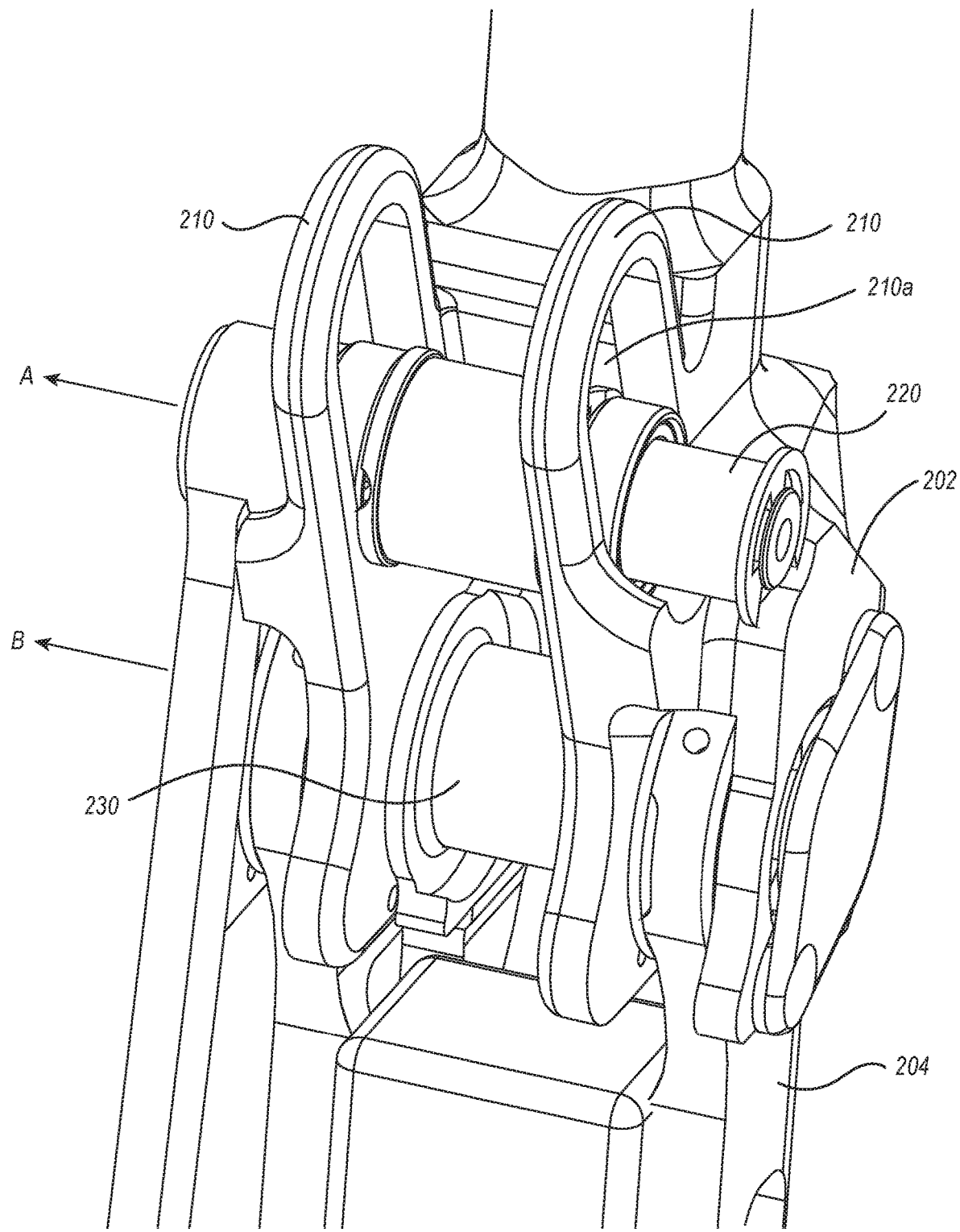
Figure 4C:
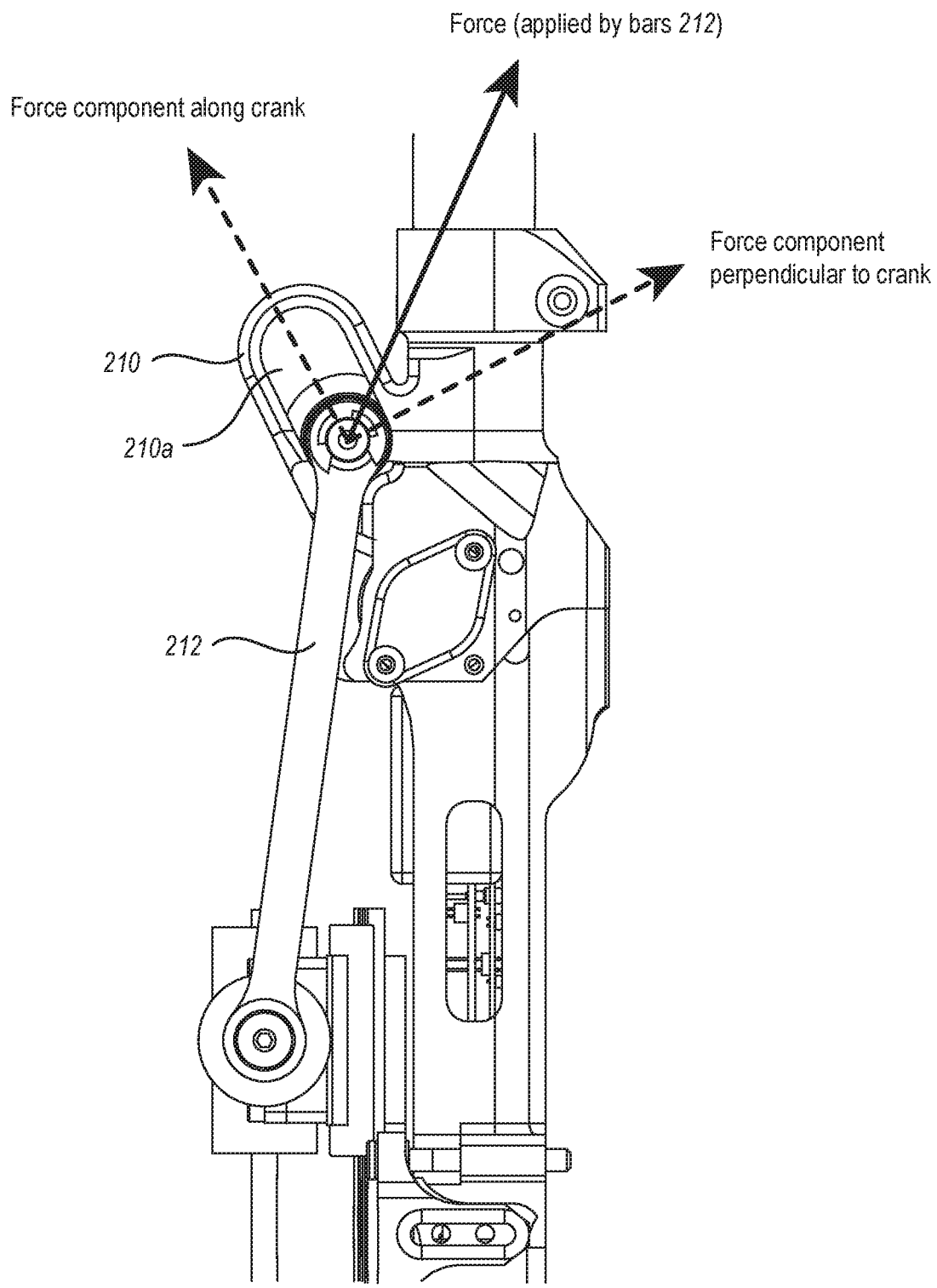

FIGS. 4A through 4C further illustrate the assistive device 201, with a focus on the function of the transmission system and passively variable element 200. In the illustrated embodiment, the passively variable element 200 is made of an elastically deformable material configured in the form of a belt having a first end looped around the pivot shaft 220, and a second end looped around a shaft 230 housed in, and fixed to, the head portion 202 (see FIG. 4B, where element 200 has been removed to illustrate underlying components). Because the pivot shaft 220 is movable relative to the shaft 230, movement of the pivot shaft 220 causes a change in the position, shape, and/or orientation, of the passively variable element 200.

More particularly, the passively variable element 200 changes configuration, position, and/or orientation when there is a change in the distance between an axis A defined by the pivot shaft 220 and an axis B defined by the shaft 230. Such a change in this distance and, thus, the extent to which the configuration, position, and/or orientation of the passively variable element 200 changes, may occur in a variety of circumstances. In general, as shown in FIG. 4C, a force applied by the bars 212 to the flanges 210 may have two components, one of which is perpendicular to the crank, and the other of which extends along the crank. The former component is responsible for pivoting the joint, while the latter component is responsible for causing a deformation and/or other change to the passively variable element 200.

For example, upward movement of the bars 212 will drive joint extension as a result of the force component perpendicular to the crank, but will also tend to stretch/extend the passively variable element as a result of the force component extending along the crank. An upward force applied by the bars 212 will therefore tend to stretch/extend the passively variable element 200 by an amount that depends on the structural and/or material characteristics of the passively variable element 200 (including, e.g., the spring constant, modulus of elasticity, etc.), and the magnitude of the force applied by the bars 212. During a locomotion task that requires high torque, such as extension of the knee joint during stair ascension, part of the upward force applied by the bars 212 will result in stretching/extending of the passively variable element 200, which will result in movement of the pivot shaft 220 further away from shaft 230, which in turn automatically provides a higher torque profile (higher torque, lower speed) more suitable for the locomotion task at hand.

Potential energy stored in the deformed passively variable element 200 may be utilized to assist in driving subsequent joint motion. For example, after joint extension during stair ascension, the deformed passively variable element 200 may compress, which moves the pivot shaft 220 closer to the shaft 230 and assists in moving the bars 212 downward to help drive joint flexion during the swing phase. This also allows the pivot shaft 220 to move to a position lower within the cutout section 210a that corresponds to a lower torque/higher speed profile more suitable to the swing phase.

In another example, a downward movement of the bars 212, whether by the user and/or by through actuation of the nut 214/screw 216, causes flexion of the joint 206 (i.e. counterclockwise rotation of the head portion 202 relative to the foot portion 204). At a certain point (e.g., once the cutout section 210a is substantially horizontal), continued downward movement of the bars 212 will cause the pivot shaft 220 to move toward the left/upper portion of the cutout section 210a. This causes the passively variable element 200 to stretch, or otherwise change configuration, position, and/or orientation. In this way, at least some of the input from the motor/user is converted to potential energy that is stored, even if only for a very short time, in the stretched passively variable element 200. When the pivot shaft 220 subsequently moves upward against the flanges 210 at the initial portion of extension, at least some of the energy stored in the stretched passively variable element 200 may be expended in assisting the motion of the pivot shaft 220 back toward the right/lower portion of the cutout section 210a. Consequently, the passively variable element 200 returns to a relatively less stretched, or less deformed, configuration.

As suggested in the foregoing discussion, embodiments are configured to receive inputs to the passively variable element(s) from the user and/or the actuation mechanism. In some circumstances, only one power source may provide an input for a particular locomotion task or portion of a locomotion task while, in other circumstances, both power sources may provide an input for a particular locomotion task or portion of a locomotion task. Thus, in some particular embodiments, movement of the pivot shaft 220 by way of the bars 212 may be performed simultaneously, or nearly so, with movement of the head portion 202 by the user, such that two inputs are provided to the passively variable element 200. In other circumstances and/or embodiments, the power inputs can be provided serially with respect to each other.

With continued reference to the configuration and arrangement of the passively variable element 200, the passively variable element 200 may be considered as a crank of variable length, whose length is at a maximum when the pivot shaft 220 is at the upper end of the cutout section 210a, and whose length is at a minimum when the pivot shaft 220 is at the lower end of the cutout section 210a. The relative position of the pivot shaft 220 determines the extent, if any, to which the passively variable element 200 changes in any way in response to an input from a power source. Put another way, the input from the power source required to operate the joint 206, whether the power source be the user and/or the actuation motor, is at a relative maximum when the pivot shaft 220 is at the lower end of the cutout section 210a, and the power source input required to operate the joint 206 is at a relative minimum when the pivot shaft 220 is at the upper end of the cutout section 210a and thus includes an amount of stored potential energy.

Other Exemplary Assistive Devices

Figure 5:
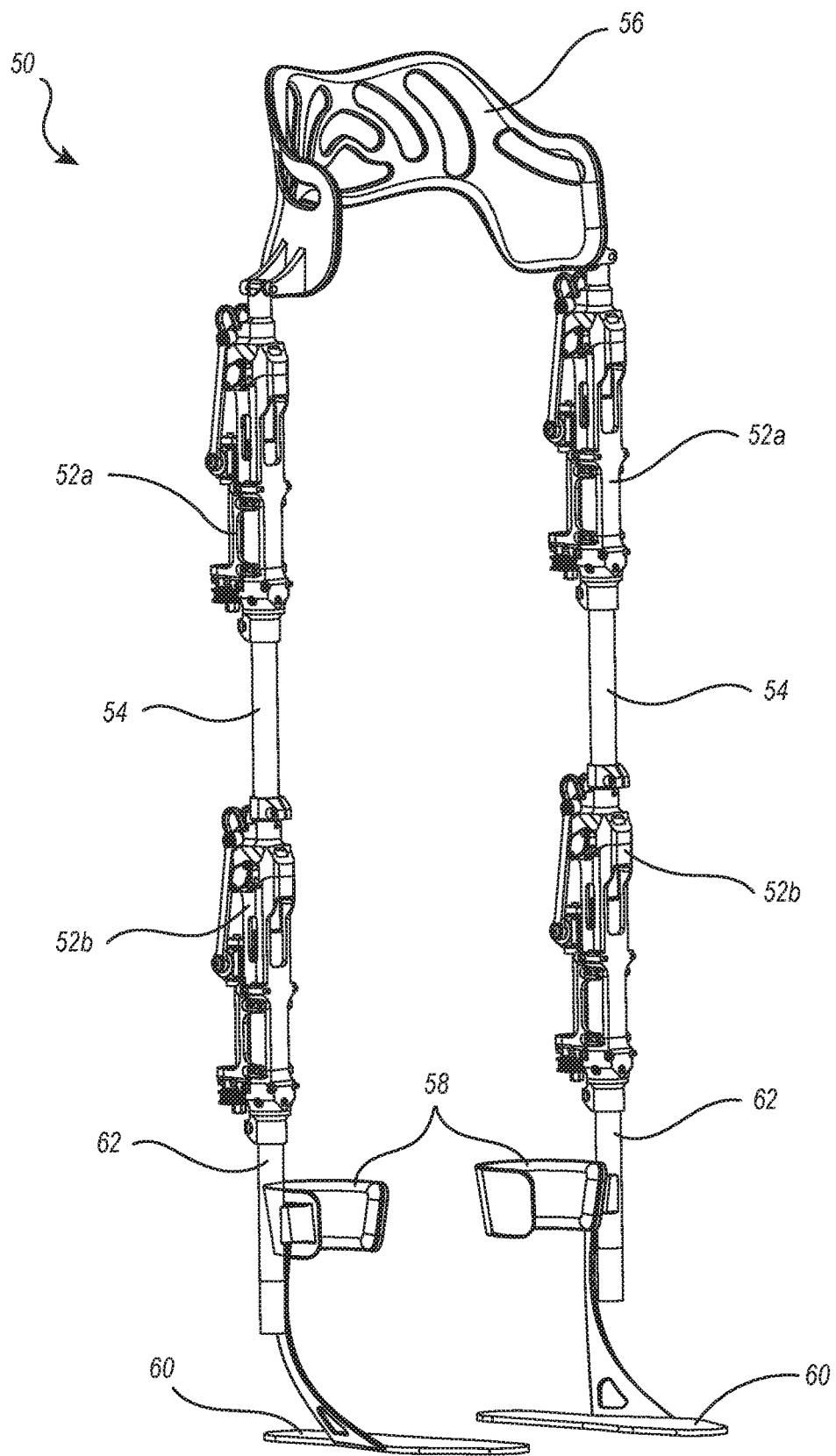
FIG. 5 illustrates a perspective view of an exemplary orthosis comprising a passively variable transmission system/mechanism.

FIG. 5 illustrates one example of an assistive hip and knee orthosis 50 which may incorporate one or more of the variable transmission systems described herein (active and/or passive). The assistive hip and knee orthosis 50 may be in the form of a dual hip and knee orthosis that includes a total of four (4) assistive orthosis subassemblies 52. Two uppermost assistive hip orthosis subassemblies 52a are configured and arranged to assist a user to bend at the hip, such as in a forward direction, while two lowermost assistive knee orthosis subassemblies 52b are configured and arranged to assist a user to operate a pair of artificial knee joints in connection with performance of a locomotion task. The hip assistive orthosis subassemblies 52a are connected to the knee assistive orthosis subassemblies 52b by respective hip-knee connection tubes 54, or comparable structures. In some embodiments, one, some, or all, of the orthosis subassemblies 52 are movable along one of the hip-knee connection tubes 54 so that the configuration of the assistive hip and knee orthosis 50 can be modified to suit the needs and anatomy of a particular user.

The assistive hip and knee orthosis 50 may include a trunk support element 56, which may be padded, configured to extend around a portion of, and support, the trunk of a user. In some embodiments, a belt or strap (not shown) can be provided to securely attach the trunk support element 56 to the user. The assistive hip and knee orthosis 50 may also include a pair of lower leg braces 58, which may be padded, configured to receive a portion of a lower leg of the user. Finally, the assistive hip and knee orthosis 50 may include a pair of foot plates 60, to which the shoe or foot of a user can be removably connected, such as by straps or belts (not shown).

In some embodiments, a lower leg brace 58 and foot plate 60 may be integral elements of a lower leg assembly that may also include an adjustment element 62, which may be tubular in form, whose position is adjustable relative to a corresponding knee assistive orthosis subassembly 52b. This configuration enables the position of the lower leg brace 58 and foot plate 60 to be adjusted to suit a particular user.

It should be noted that the assistive hip and knee orthosis 50 is presented only by way of example and yet another embodiment of the invention is directed particularly to an assistive orthosis that includes an artificial joint, such as a human knee joint, but does not include a hip assistive orthosis subassembly, or trunk support element. As well, at least some embodiments of an assistive orthosis that includes an artificial joint, such as a human knee joint, are configured such that they omit one or both of a lower leg brace and foot plate.

Figure 6A:
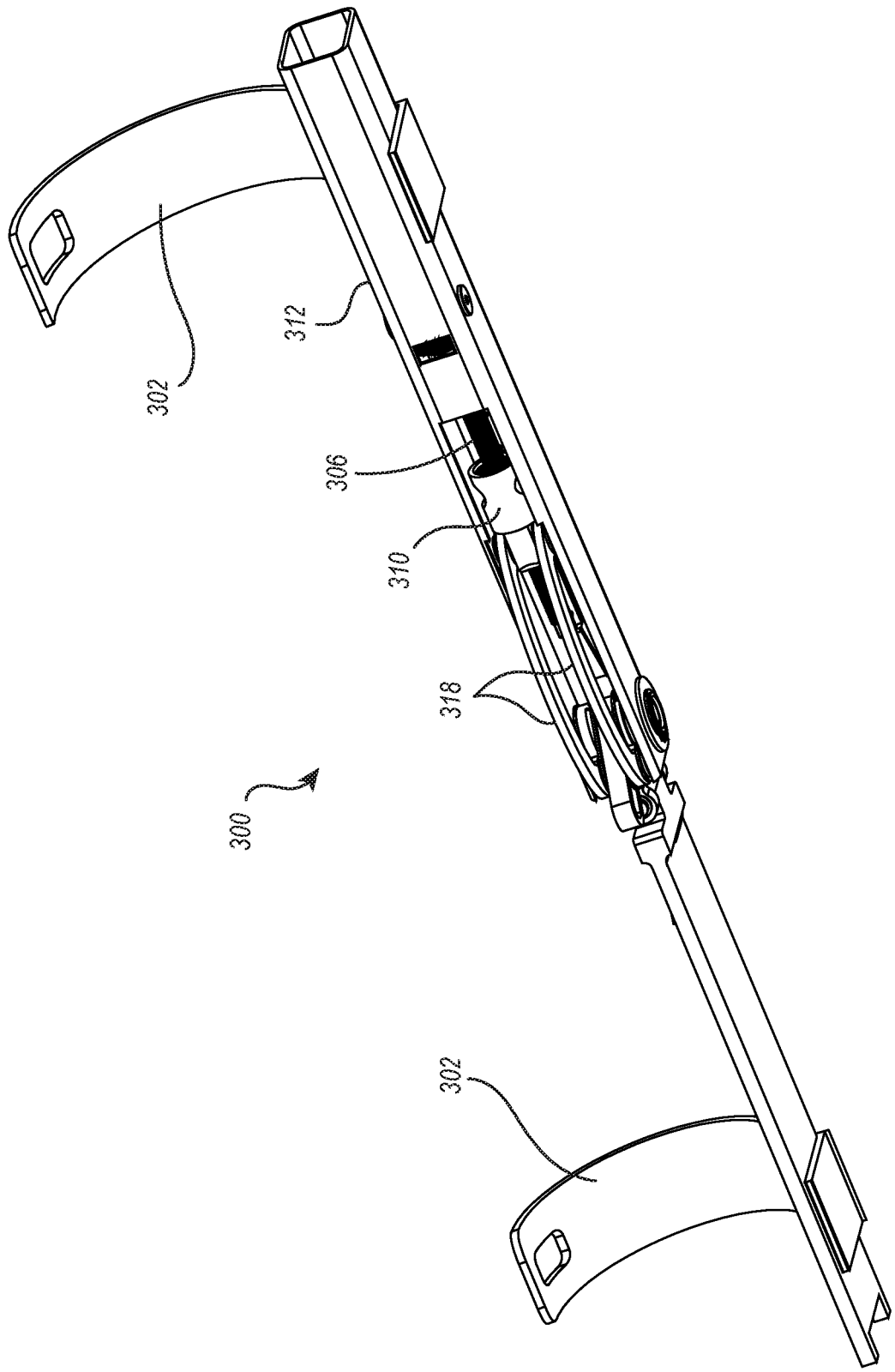
FIGS. 6A through 6C illustrate exemplary orthoses comprising a passively variable transmission system/mechanism.
Figure 6B:
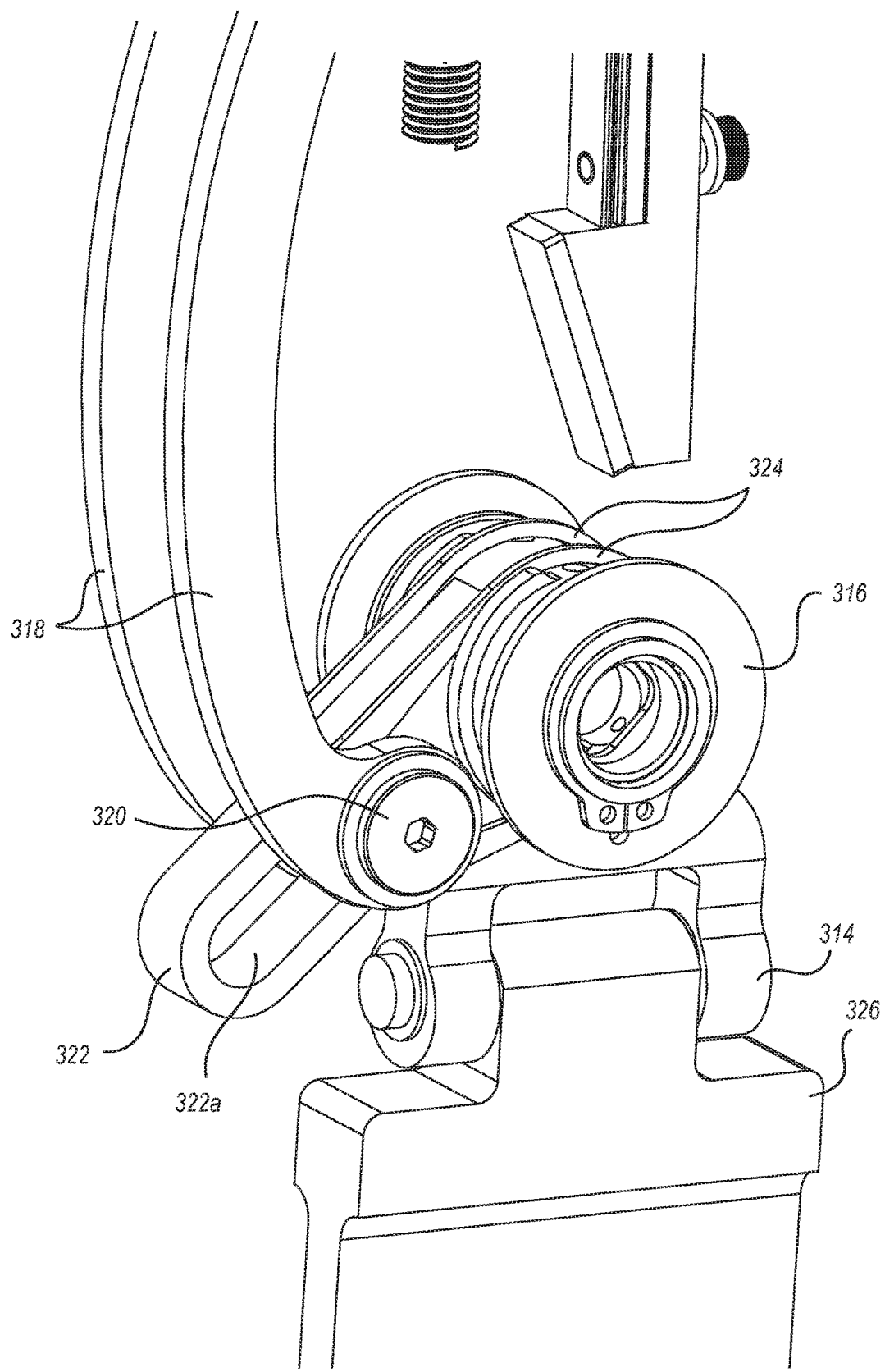
Figure 6C:
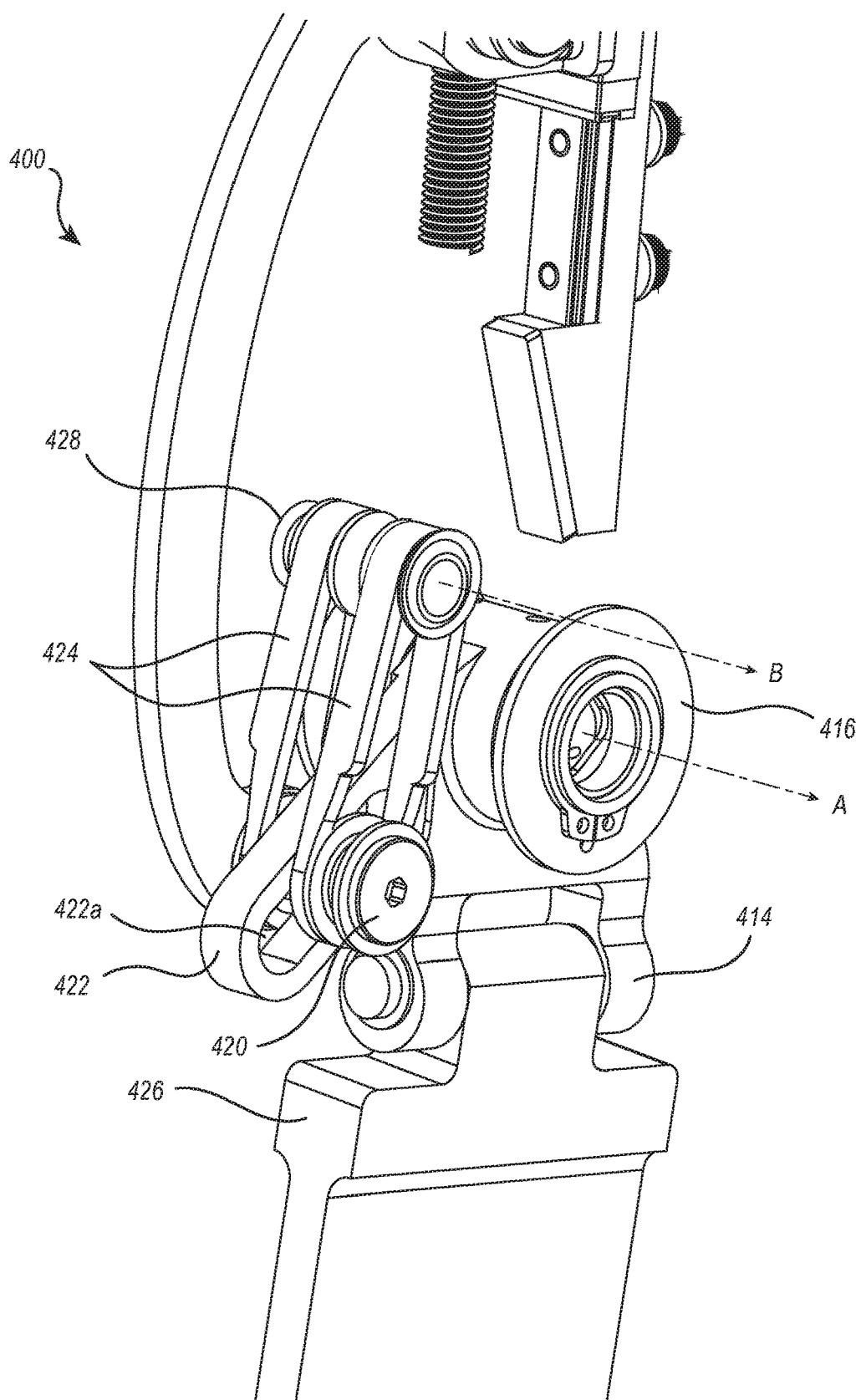

With attention now to FIGS. 6A through 6C, details are provided concerning another embodiment of an assistive device having a passively variable transmission system, two examples of which are denoted generally at 300 and 400, respectively. These particular embodiments integrate a passively variable transmission system with an assistive orthosis. As these two embodiments include features that are similar, or identical, in many regards to other embodiments disclosed herein, the following discussion is focused primarily on differences between the assistive prostheses 300 and 400, and the other disclosed embodiments.

Turning first to FIG. 6A, the assistive orthosis 300 may include a cuff 302, or comparable device, configured to be temporarily connected with, and to support, a portion of an upper leg of the user, such as the front of the thigh of the user. The cuff 302 may include straps (not shown) and/or other elements that enable the cuff 302 to be releasably secured to the upper leg of the user. Such straps and elements may be configured so that the cuff 302 can be tightened and loosened as desired. Another cuff 302 at the lower end of the assistive orthosis 300 is configured to be temporarily connected to a portion of a lower leg of the user, such as the front of a shank of the user.

Similar to other disclosed embodiments, the assistive orthosis 300 may include a motor (e.g., hidden from view within frame 312) that is connected with a screw 306 such that operation of the motor is effective to rotate the screw 306 in first and second opposing directions. The motor can be connected to the screw 306 in any manner, and with any power transmission component(s) known in the art, effective to enable operation of the motor to rotate the screw 306.

The assistive orthosis 300 includes a threaded nut 310 that is configured to move along the screw 306 in response to rotation of the screw 306. As the operation of the nut 310 is similar, or identical, to the other embodiments disclosed herein, a detailed discussion of the nut 310 is not provided here. Part or all of the nut 310, screw 306, motor, and gear arrangement may be housed within a frame 312. The frame 312 may be open at the back to enable free movement of various components of the assistive orthosis 300, and also to enable ready access to components for adjustment, maintenance, and/or replacement.

The frame 312 can be made of any of the materials disclosed herein, and may have a generally hollow or tubular construction, and the cuff 302 may be connected to the frame 312. As best shown in FIG. 6B, which is an expanded view of a portion of the orthosis 300 with the frame 312 removed for better visualization, the assistive orthosis 300 includes a plate 314 to which bars 318 and other components of the frame 312 are rotatably connected. As such, the plate 314 and frame 312 together define a rotatable joint 316. The plate 314 may be a single piece structure that may be machined, cast, and/or otherwise formed out of one or more metals. The plate 314 may alternatively be made of plastic, composites, or any of the other materials disclosed herein.

In some implementations, the plate 314 may be a "top" plate located on the upper portion of the orthosis 300 (e.g., against the user's thigh) while the frame 312 represents the "bottom" portion of the orthosis 300 (e.g., against the user's shank). These relative positions may be reversed, however, without affecting the function of the rotatable joint 316, so long as the rotatable joint 316 is aligned with the corresponding joint of the user.

With particular reference to FIG. 6B, the assistive orthosis 300 also includes a pair of bars 318. In the illustrated embodiment, the bars 318 are curved, although that example configuration is not necessarily required. The bars 318 may be made of any of the materials disclosed herein. The bars 318 are rotatably connected at their upper ends to the nut 310, and arranged to be parallel to each other. The respective lower ends of the bars 318 are rotatably connected to respective ends of a pivot shaft 320 that extends through, and is movable along, a longitudinal cutout section 322a of a flange 322 that, in some embodiments, is integral with the plate 314.

In general, movement of the pivot shaft 320 toward the plate 314 presses against the flanges 322 and causes flexion of the rotatable joint 316. On the other hand, movement of the pivot shaft 320 away from the plate 314 presses against the flanges 322 and causes extension of the rotatable joint 316.

Movement of the pivot shaft 320 along the longitudinal cutout section 322a may be constrained, or compelled, depending upon the circumstances, by one or more passively variable elements 324. In the illustrated embodiment, two passively variable elements 324 are provided, and are arranged on respective sides of the flange 322, each wrapping around the pivot shaft 320 at one end and wrapping around a shaft defining the rotation of the joint 316 on the other end. More, or fewer, than two passively variable elements may be employed in other embodiments. As such, an axis of rotation of the second ends of the passively variable elements 324 is coincident with an axis of rotation of the artificial joint 316. As explained below in connection with an example alternative embodiment however, the axis of rotation of the second ends of the passively variable elements 324 can, instead, be offset from an axis of rotation of the artificial joint 316.

As shown, the top plate 314 may be rotatably connected to a connection plate 326 to which a cuff 302 is connected. This rotatable connection of the top plate 314 to the connection plate 326 may serve as an abduction/adduction joint to prevent misalignment of the portions of the assistive orthosis 300 and, thus, the leg portions of the user to which the assistive orthosis 300 is attached.

Operationally, the assistive orthosis 300 may be similar, or identical, to other embodiments disclosed herein. For example, an input from the motor and/or the user may serve to drive flexion/extension of the artificial joint 316. As well, forces applied by the bars 318 have a component that elastically may deform the passively variable elements 324 and cause movement of the pivot shaft 320 within the cutout section 322a, allowing dynamic adjustment of the corresponding torque profile. Additionally, when the input from the motor and/or user is removed, or reduced, the passively variable elements 324 may tend towards their undeformed state, thereby readjusting the torque profile and also releasing stored potential energy which may aid in moving the artificial joint 316.

Turning now to FIG. 6C, reference is briefly made to the assistive orthosis 400. Except as noted in the following discussion, the assistive orthosis 400 may be identical in its configuration and operation to the orthosis 300, with similar/identical components having like reference numerals. In the view of FIG. 6C, one of the bars has been removed to better illustrate the visualized componentry.

As shown, the respective second ends of the passively variable elements 424 are disposed about a shaft 428 that may be mounted to the frame as opposed to being directly disposed within the portion of the plate 414 deforming the axis of rotation 'A'. As a result of this configuration and arrangement, an axis 'B' of rotation of the second ends of the passively variable elements 424 is offset from the axis 'A' of rotation of the artificial joint 416. In general, the axes 'A' and 'B' may, or may not, be offset from each other as dictated by the needs of a particular application. Likewise, the extent of any such offset may vary from one embodiment to another. In some embodiments, the shaft 428 may be adjustable/movable along a slot (not shown) formed in the frame of the device, and may optionally be lockable into a desired position within the slot, so that the offset between axes 'A' and 'B' may be selectively varied.

Operationally, the assistive orthosis 400 performs in the same way as the assistive orthosis 300. However, due to the offset of axes 'A' and 'B,' the two assistive prostheses 300 and 400 may have different respective torque and speed characteristics.

Passively Variable Transmission System Variations

With reference now to FIGS. 7A through 7I, further details and features of some example embodiments are disclosed and schematically illustrated. It should be understood that the features of any particular group of one or more figures may be combined to define still other embodiments. While these embodiments are shown here in schematic form, it will be understood that the features and concepts of these embodiments may be readily applied to an artificial joint in an assistive device such as with any of the devices disclosed herein.

Figures 7A, 7B, 7C:
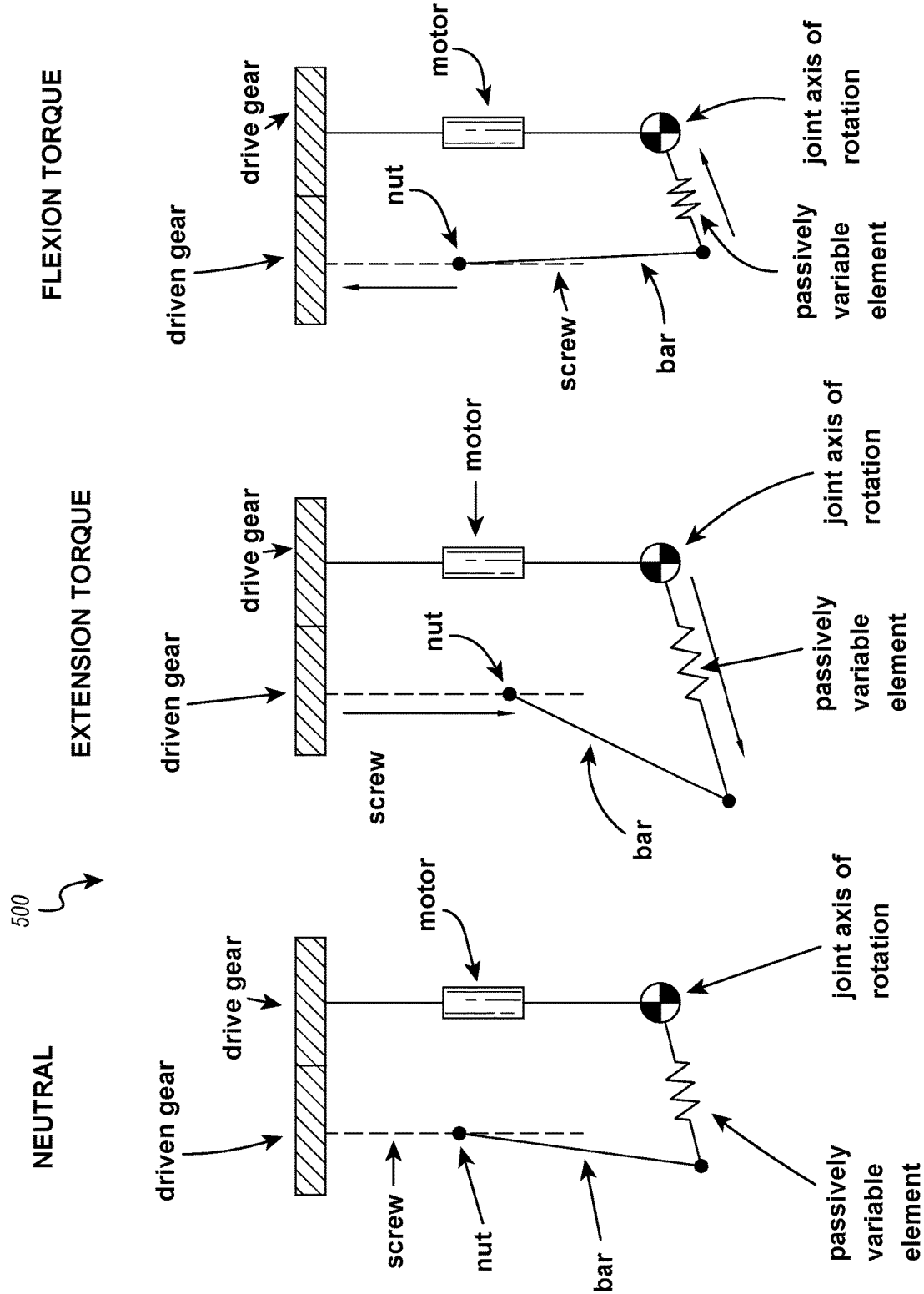

With reference first to FIG. 7A through 7C, one or more embodiments, denoted generally as 500, may be configured to assume at least three different states, that is, a neutral state, an extension state, and a flexion state. In the illustrated example, the crank comprises one or more passively variable elements. When in the neutral state, the assistive prosthesis 500 is configured such that the passively variable element(s) are undeformed, or only slightly deformed. In the extension state, the position of the nut has been changed so that the one or more passively variable elements are elastically deformed, or elongated. This adjusts the crank length and therefore provides an adjusted torque profile to the device.

As noted herein, in some embodiments, the extension state may be achieved without any motion of the nut. That is, the stored potential energy in the passively variable elements may be utilized at least in part to aid in subsequent movement of the artificial joint, thus minimizing or eliminating the need for work applied by the user and/or the motor to the artificial joint during the subsequent movement. In the flexion state, the position of the nut has been changed so that the one or more passively variable elements are elastically deformed, or compressed.

Figure 7D:
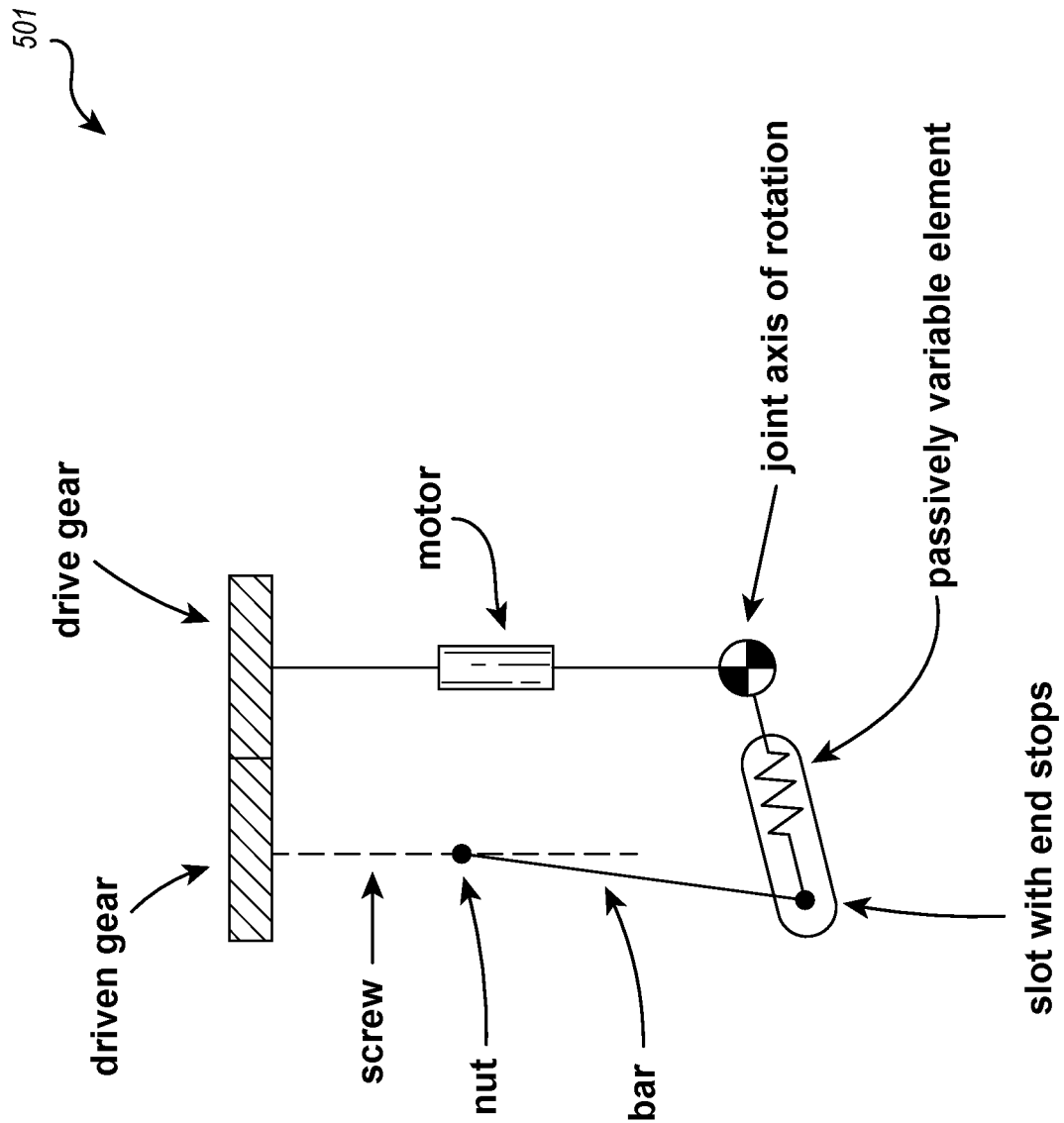

Turning now to assistive device 501 of FIG. 7D, the maximum and/or minimum extent to which a passively variable element can be elastically deformed can be defined by appropriate configuration of the assistive prosthesis. For example, stops or other mechanisms could be positioned on or in a longitudinal cutout section of a flange so as to limit the range of motion of the pivot shaft and, thus, the extent to which the connected passively variable elements are deformed during operation. In some embodiments, the position of such stops or other mechanisms is adjustable so that, within an embodiment, a user or other person can change the extent to which the connected passively variable elements are deformed during operation. In an alternative arrangement, static or movable stops may be provided along the screw to limit travel of the nut and, thus, the extent to which the connected passively variable elements are deformed during operation. As a further example, the length of the longitudinal cutout section can be selected to define the extent to which a passively variable element can be deformed. As another example, a curved, rather than longitudinal, cutout section may be employed in a flange to define the extent to which a passively variable element can be deformed, and/or to achieve various other effects concerning the operation of the assistive prosthesis.

With reference next to FIGS. 7E and 7F, two example arrangements of an assistive prosthesis 502 are disclosed. In general, FIG. 7E discloses that, in one or more embodiments, the cutout section and/or the passively variable element may not be coincident with the axis of rotation of the artificial joint. In more detail, and with reference to FIG. 7E, it can be seen that while a longitudinal axis of the slot is aligned with the axis of rotation of the artificial joint, the axis of motion of the passively variable element is offset from the axis of rotation of the artificial joint. In contrast, and with reference now to FIG. 7F, it can be seen that the longitudinal axis of the slot is offset from the axis of rotation of the artificial joint, while the axis of motion of the passively variable element is aligned with the axis of rotation of the artificial joint.

Figure 7G:
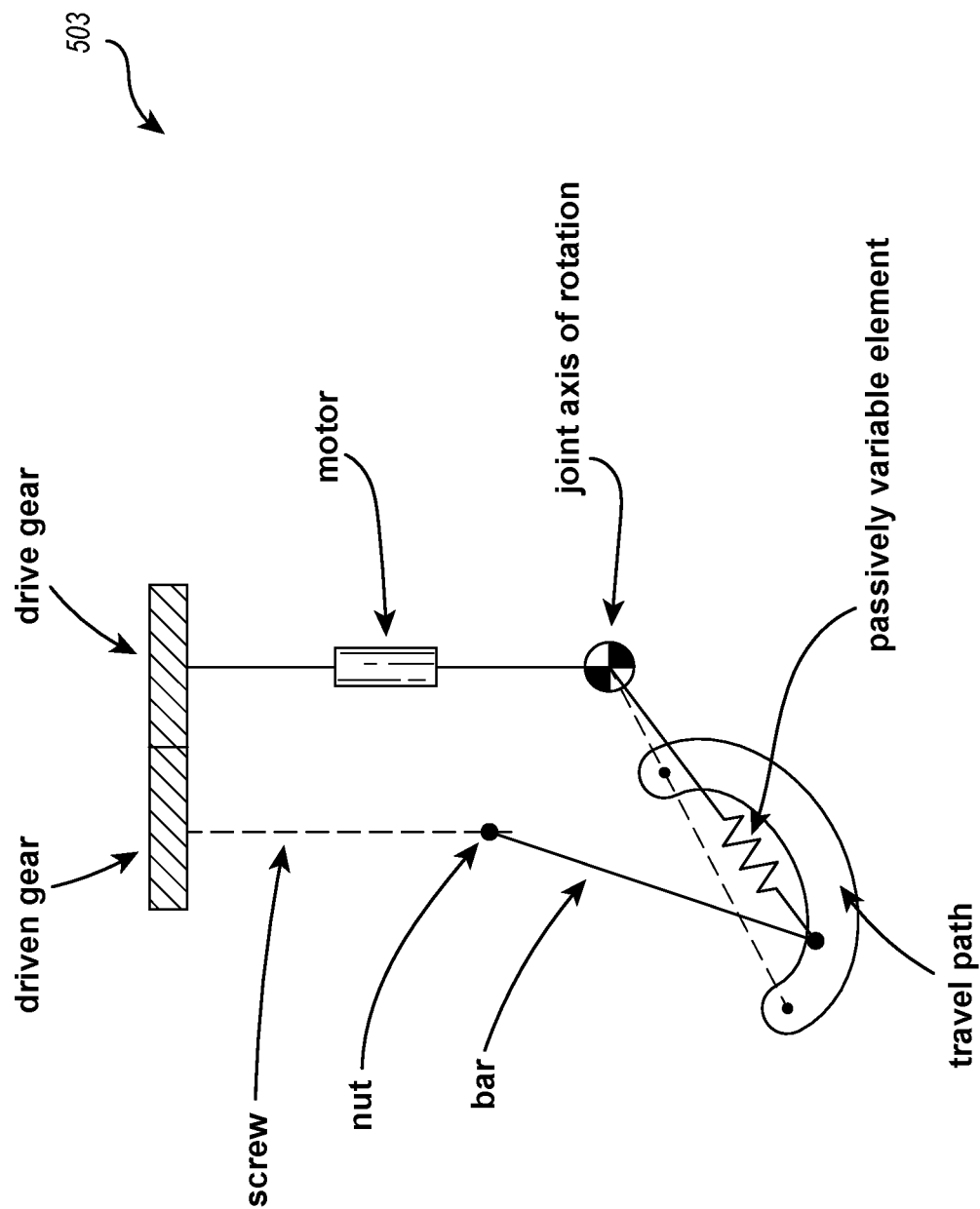

Turning now to FIG. 7G, it can be seen that in some embodiments, an end of the passively variable element connected to the bar(s) can travel along a curved path, rather than along a straight path as is the case in some of the other disclosed embodiments. Variables such as the length and radius of curvature of the curved path can be selected in accordance with the requirements of a particular embodiment. Moreover, the curve described by the path may, but need not necessarily, be a circular curve. In other embodiments, a parabolic curve or elliptical curve, for example, may be used for the shape of the curved path. More generally, any type of curved path may be employed in one or more embodiments of the invention. Finally, in some embodiments, the path may include both a curved portion and a straight portion.

Figure 7H:
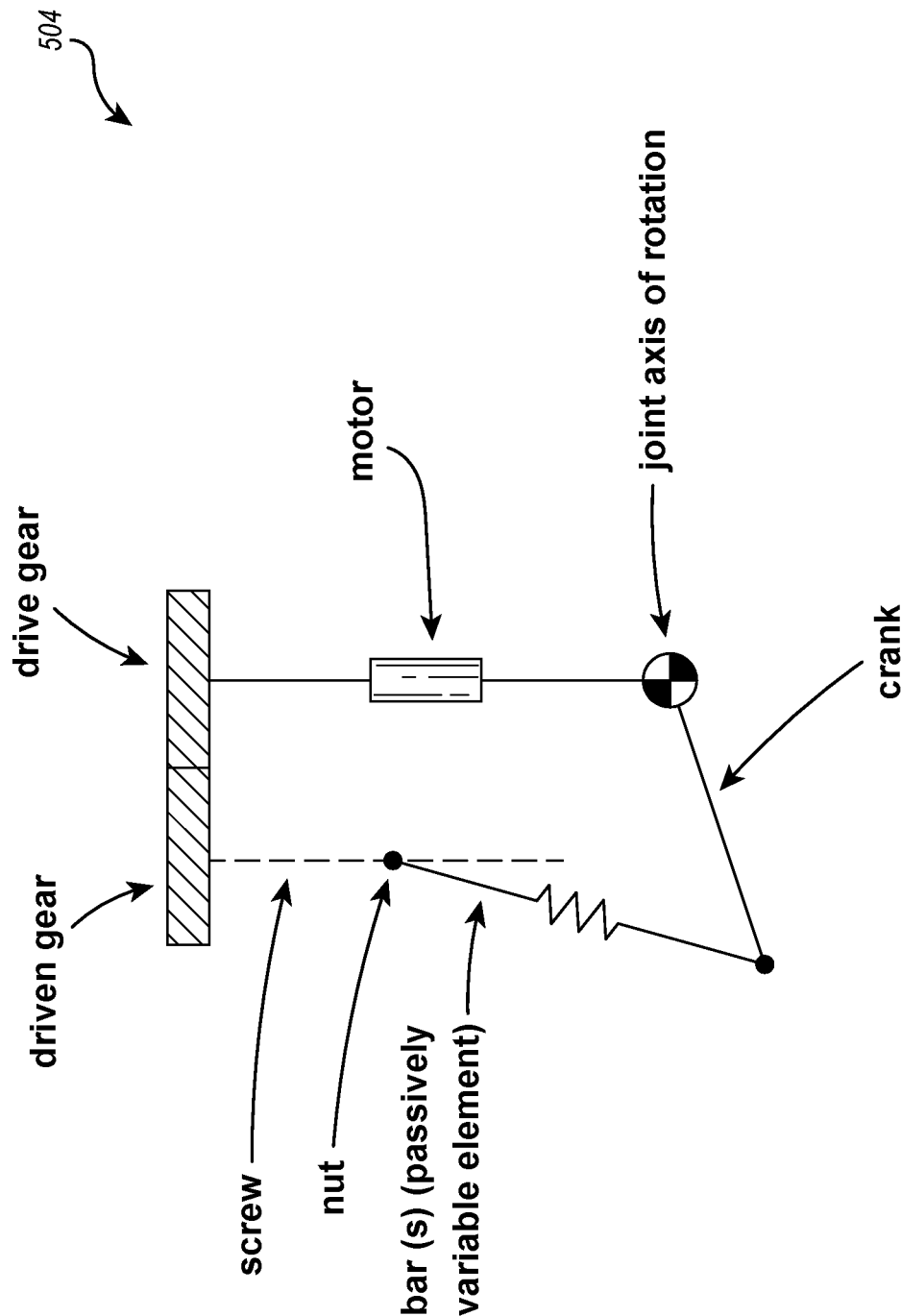
Figure 71:
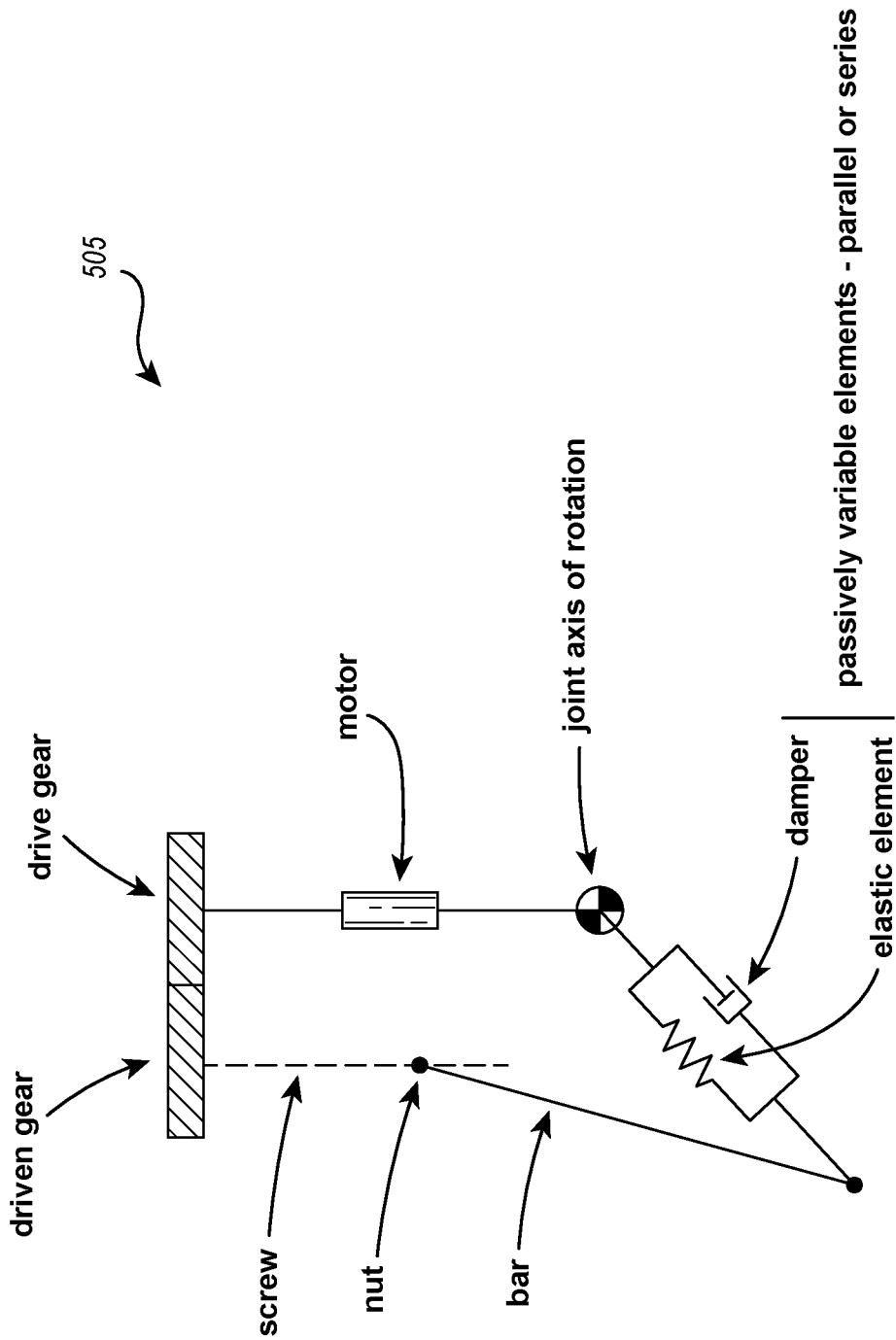

Thus far, many example embodiments have been disclosed as including a crank that comprises one or more passively variable elements. The example device 504 of FIG. 7H represents a different approach. In particular, the device 504 includes a crank that does not deform during operation. Instead, in this embodiment, the bar(s) that connect the movable nut to the crank comprise one or more passively variable element(s). Because the bar(s) are connected to the nut, the bar(s) elastically deform in response to movement of the nut along the screw. In this example, the end of a bar that is connected to the nut is movable in unison with the nut, while the other end of the bar is fixed in position, as shown.

With reference now to the example embodiment of FIG. 7I, and as disclosed elsewhere herein, one or more embodiments of the invention may include multiple passively variable elements. The multiple passively variable elements can be arranged in a variety of ways, such as in series for example, or in parallel. Moreover, one or more embodiments may include multiple passively variable elements that are all of the same type, such as elastically deformable bands for example. Still other embodiments may include multiple passively variable elements that are of different types. For example, and as shown in FIG. 7I, one or more embodiments may include a damper as well as an elastically deformable band, and the damper and elastic band can be arranged in series, or in parallel.

EXAMPLES

Example 1—Comparative AVT Crank Lengths

The kinematics of a lightweight assistive knee can be modelled as an offset slider-crank mechanism with an added prismatic joint along the crank. The transmission ratio thus depends on the crank length. A short crank setting would result in a low transmission ratio. Thus, it would be appropriate for activities that require high speed and low torque. On the other hand, a large crank setting would result in a high transmission ratio, which will be used for tasks that require high speed and low torque.

An analysis of healthy human biomechanics is helpful in selecting appropriate transmission ratios for different ambulation tasks, which will guide the selection of different crank lengths. The torque and speed requirements for the knee joint were extracted from healthy biomechanics using an available dataset. Generally, walking requires 66% lower torque and 37% higher speed than ambulation on stairs. Within stair ambulation, ascent and descent are also different, with the latter requiring 19% higher torque and 21% lower speed.

To select appropriate transmission settings (i.e., length of the crank) for each ambulation mode, we developed a dynamic simulation framework that takes as input the required knee torque and speed and computes the required motor torque and speed and the load on the structural components. Notably, the simulation framework includes the dynamic effect of the motor, primary timing-belt transmission and secondary roller screw transmission. Also, a 10% loss in the device's mechanics (2.6% in timing belt, 6.3% in the screw system, and 0.9% in joint friction) is accounted for. Two key boundaries were considered in the simulations: (1) the hard limit of the motor torque-speed curve imposed by the available voltage on the motor windings (i.e., 21.6V as imposed by the 6-cell battery) and (2) the motor thermal limitations due to Joule heating (i.e., 8.4 A maximum continuous current). The estimates of the loads on the structural components were considered in a secondary design phase focused on the selection of off-the-shelf parts (i.e., rollerscrew, transmission leadscrew, ball bearings) and the design of custom components (i.e., crank, prosthesis frame).

Figure 8C:
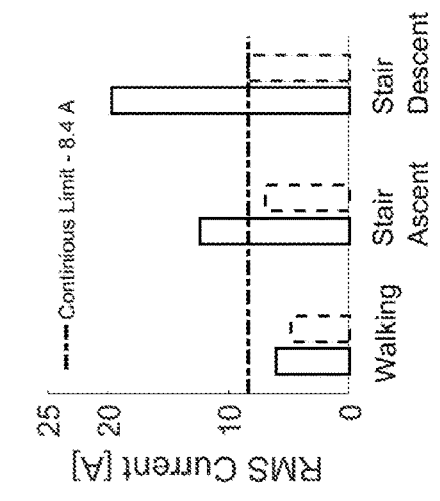
FIGS. 8A through 8C illustrate data related to different crank lengths of an actively variable transmission system in an exemplary powered knee joint prosthesis.
Figure 8A:
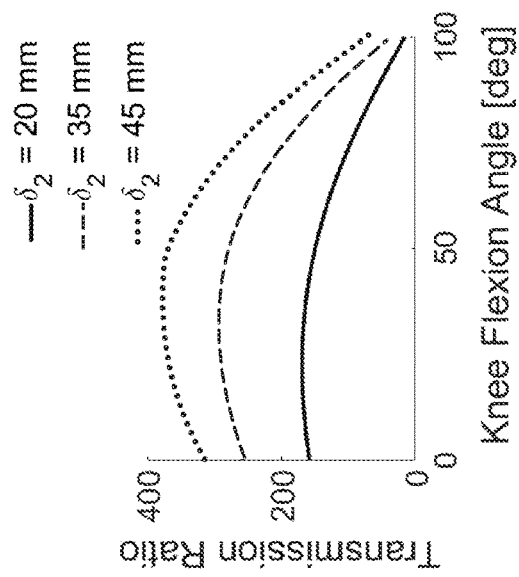
Figure 8B:
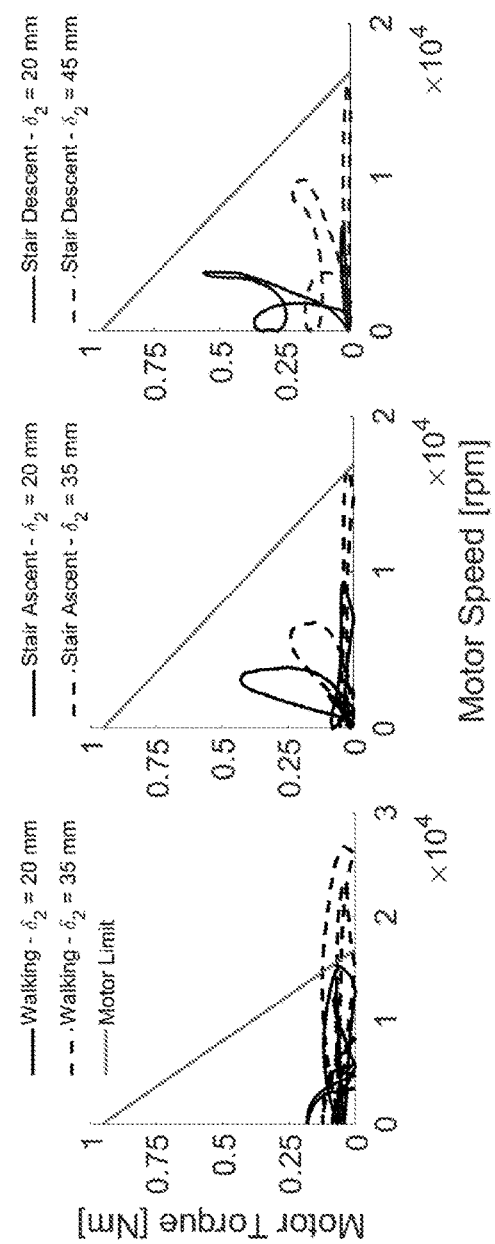

Based on the simulation outcomes, we selected an appropriate crank setting for each ambulation task, which was 20, 35, and 45 mm for walking, stair ascent, and stair descent, respectively. FIG. 8A illustrates the variation in transmission ratio over knee flexion angles for the different crank lengths (62). FIG. 8B shows the motor speed-torque curves for the different ambulation activities and crank settings, superimposed to the motor speed-torque characteristics at the maximum available winding voltage. FIG. 8C shows the resulting current RMS, which is compared to the maximum continuous motor current to provide a visual representation of the thermal limitations involved.

As can be seen, a 20-mm crank satisfies both the torque-speed requirements and the thermal limitations for walking, whereas a 35-mm crank would not be able to provide the required speed. Both a 20-mm and a 35 mm crank would provide enough torque and speed as necessary to ascend stairs. However, the smaller crank setting (20 mm) would not be able to satisfy the thermal requirements as the required rms current would be higher than the maximum continuous limit (i.e., 12.3 A). Similarly, both a 20-mm crank and a 45-mm crank would provide enough speed and torque to descend stairs. However, the rms current is 19.61 A at the 20-mm crank, and only the 45-mm crank would be able to do it continuously.

Example 2—Motor Simulations with and without PVT

Turning to FIGS. 9A through 9F, aspects of various motor simulations are disclosed that illustrate benefits of one or more embodiments disclosed herein. It is noted that the broken lines in each graph of FIGS. 9A through 9F indicate simulated operation of one or more embodiments of the invention that include one or more passively variable elements, while the solid lines in each graph indicate, for the purpose of comparison, the simulated operation of a prosthesis configured without any passively variable elements.

Figures 9A, 9B:
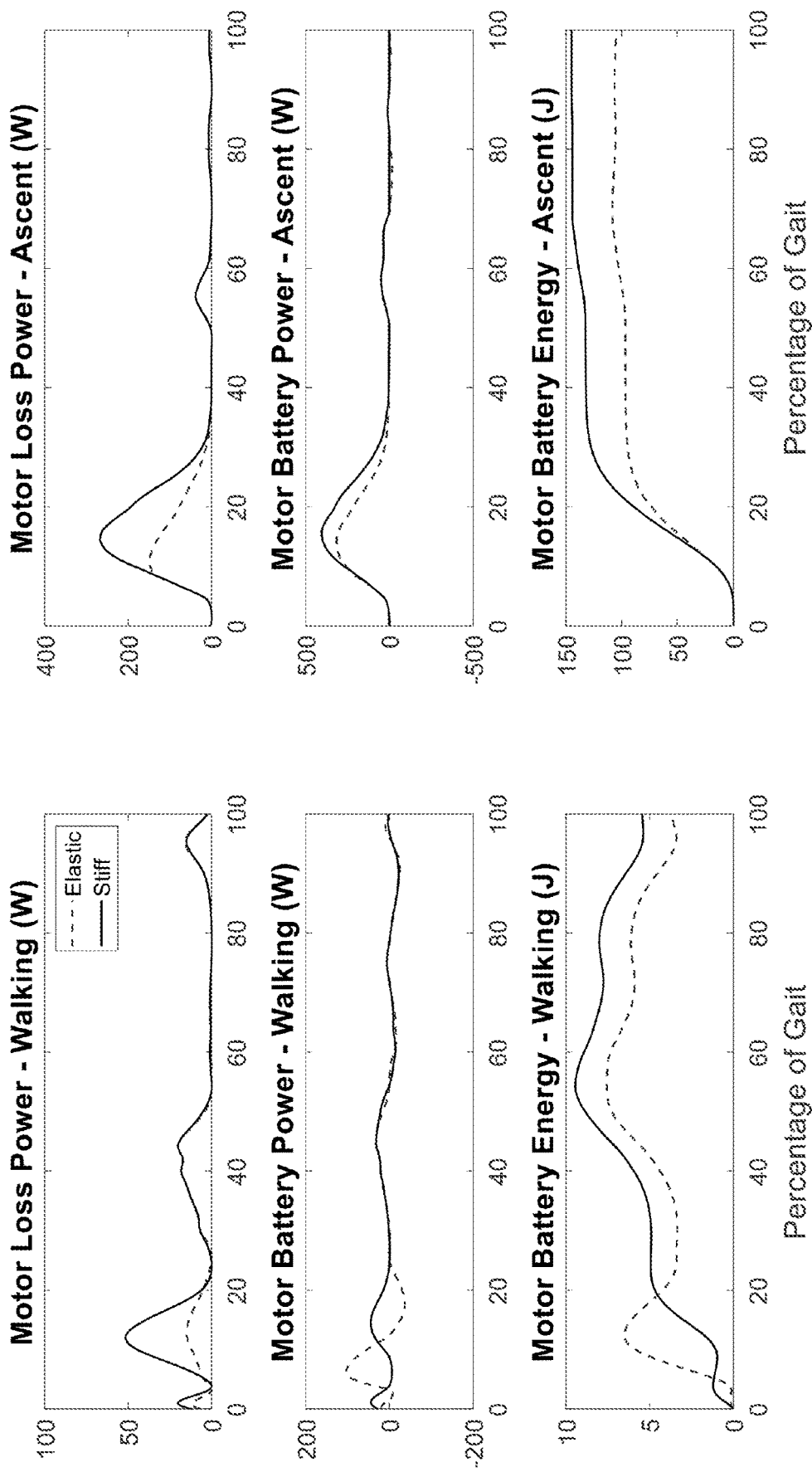
FIGS. 9A through 9F illustrate data for torque and motor performance comparing a device having a passively variable transmission system/mechanism to one that omits a passively variable transmission system.

For example, and with reference to FIGS. 9A and 9B, inasmuch as embodiments of the invention employ one or more passively variable elements that assist in operation of the assistive prosthesis, such embodiments may enable relative reductions in battery power consumption, and heat generation. As is apparent from FIGS. 9A and 9B, significant improvements may be realized by embodiments of the invention in all of the energy and power parameters, and over a range of locomotion tasks, and gaits.

Figure 9D:
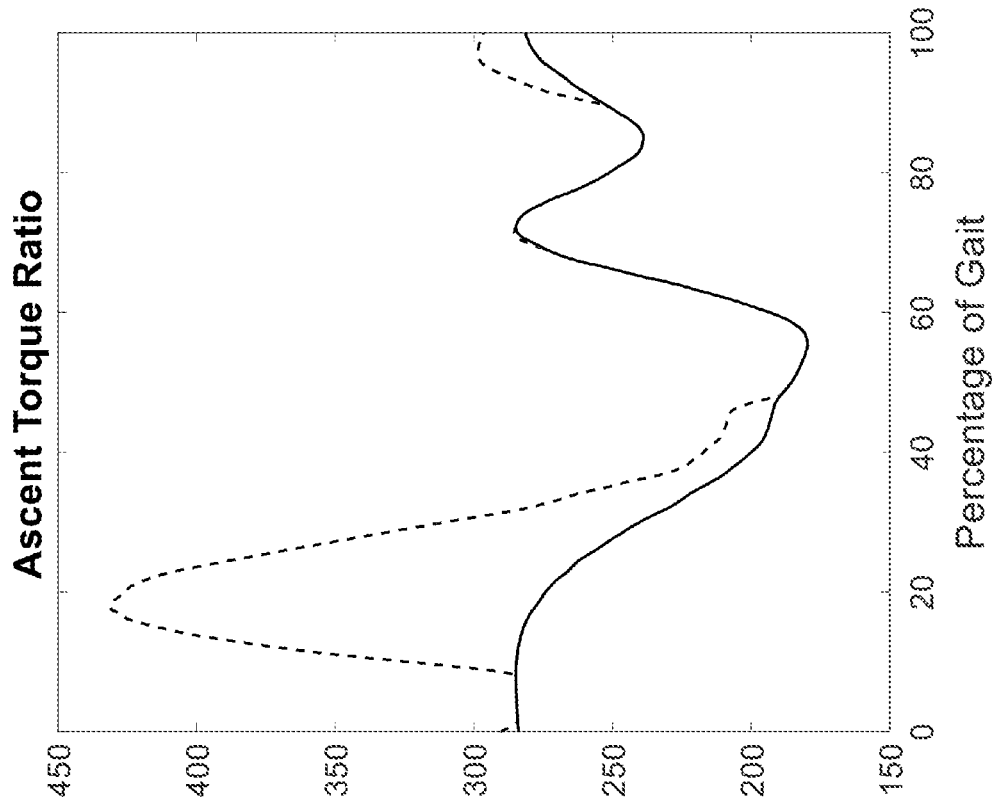
Figure 9C:
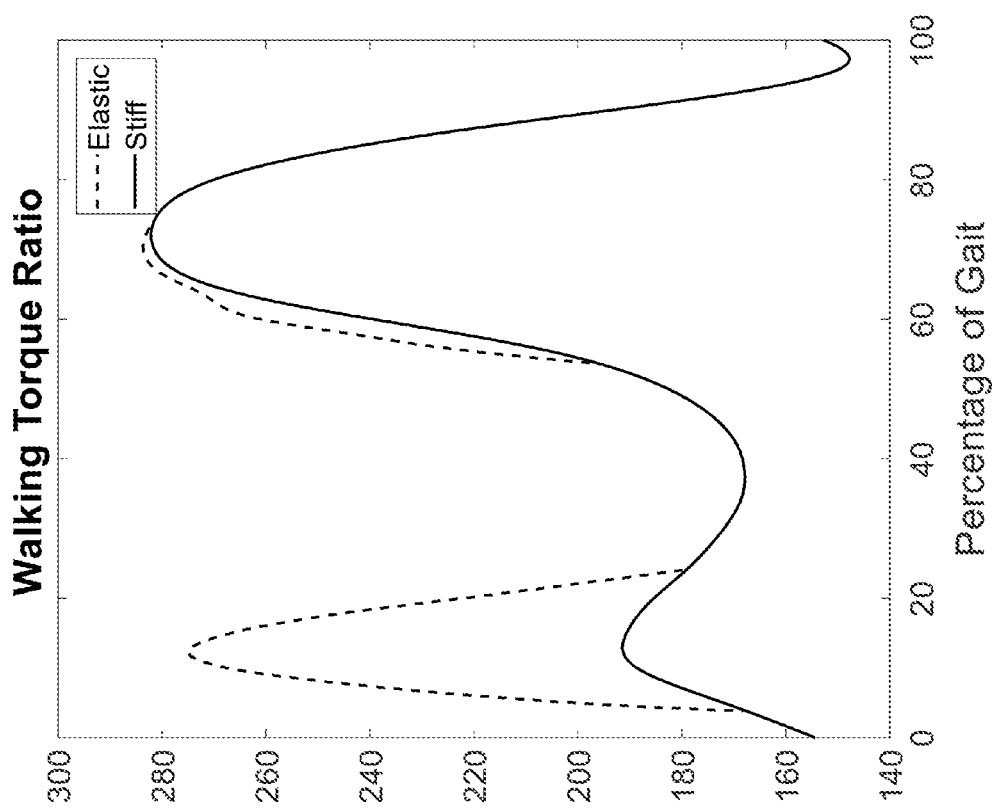

With reference to FIGS. 9C and 9D, information is disclosed concerning the torque performance of the simulated operation of one or more embodiments of the invention. As can be seen the performance of the embodiment is at least comparable to, and in some cases significantly better than, the torque performance of a prosthesis that does not include any variable elements. In particular, one or more embodiments of the invention may provide a significant increase in torque ratio during high-torque and high-power phases of operation of the assistive prosthesis.

Figure 9F:
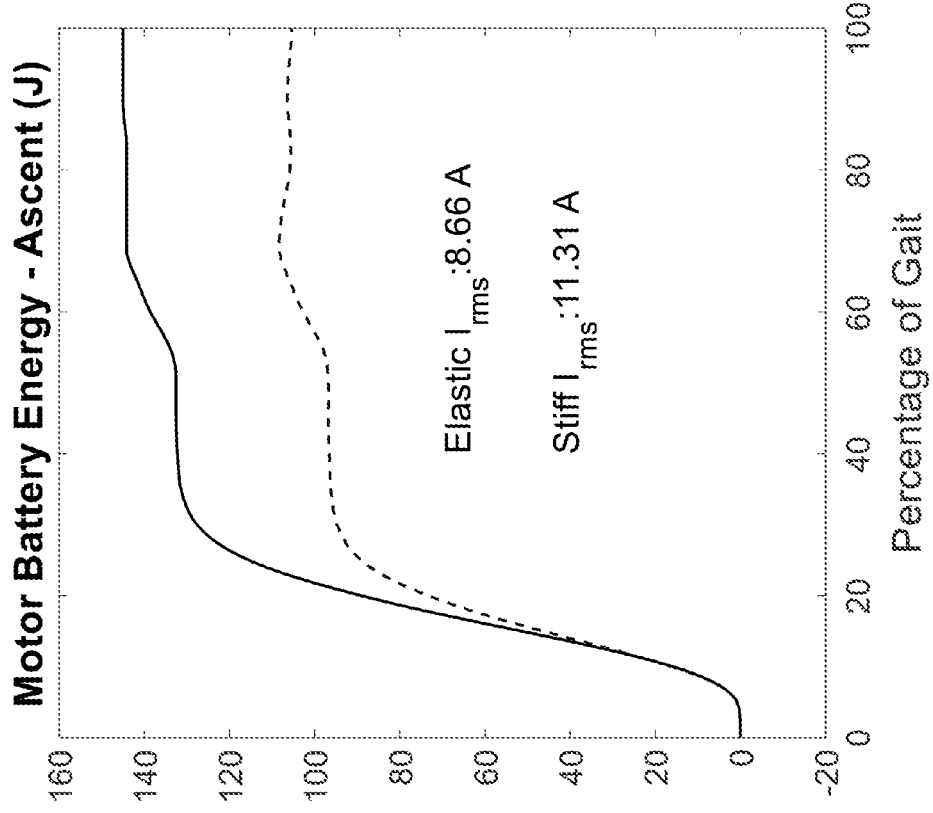
Figure 9E:
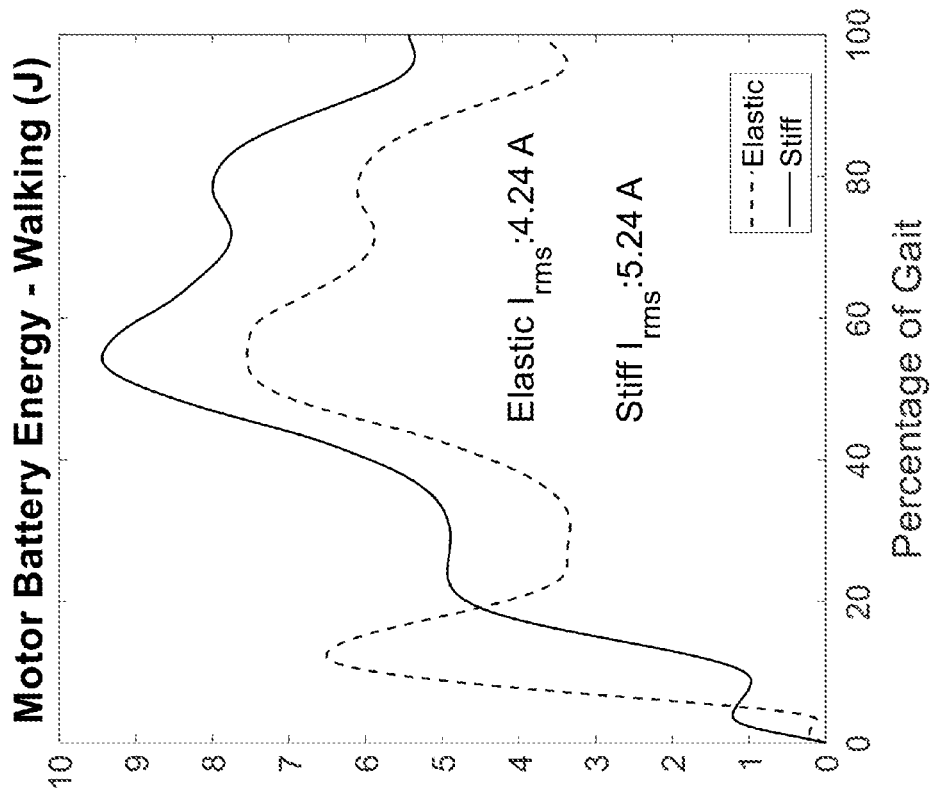

Turning now to FIGS. 9E and 9F, it can be seen that energy consumption by the motor during a simulated operation of one or more embodiments is significantly lower than the energy required to operate the motor of a prosthesis that lacks any passively variable elements. This is true for most, or all, of the range of the gait. Thus, significant energy savings may be realized by embodiments of the invention, which in turn results in extended battery life and operating time of the assistive prosthesis.

The invention claimed is:

1. An assistive device, comprising:
an artificial joint;
an actuation mechanism coupled to the artificial joint and operable to rotate the artificial joint;
a first motor configured to operate the actuation mechanism; and
a transmission mechanism coupled to the artificial joint, the transmission mechanism including a crank having a variable configuration such that in a first configuration of the crank, in which the crank has a first crank length, the artificial joint is configured to operate at a first torque profile and a first speed profile, and in a second configuration of the crank, in which the crank has a second crank length, the artificial joint is configured to operate at a second torque profile and a second speed profile that are different from the first torque profile and the first speed profile, respectively, wherein the crank comprises a pivot shaft that is movable about and between a first position in which the crank is in the first configuration and a second position when the crank is in the second configuration,
wherein the transmission mechanism comprises a passively variable element that is connected to the artificial joint and to the actuation mechanism, wherein the passively variable element is variable as the crank moves between the first and second configurations in response to a power input, wherein the passively variable element is configured to store potential energy as a result of varying in response to the power input, and is operable to assist in powering rotation of the artificial joint through release of the stored potential energy,
wherein the passively variable element extends to the pivot shaft of the transmission mechanism.

2. The assistive device as recited in claim 1, wherein the crank has a variable length.

3. The assistive device as recited in claim 2, wherein a torque profile at which the artificial joint is operable is at a maximum, with maximum torque and minimum speed, when the crank length is at maximum.

4. The assistive device as recited in claim 1, wherein the actuation mechanism and the transmission mechanism are operable independently of each other.

5. The assistive device as recited in claim 1, wherein the actuation mechanism comprises:
a flange that is connected to the artificial joint and defines a longitudinal cutout section, wherein the pivot shaft extends through the longitudinal cutout section of the flange;
a nut mounted for lengthwise movement along a screw that is connected to the first motor such that rotation of the screw by the motor causes translational movement of the nut along the screw; and
a bar that is rotatably connected to the nut and is also rotatably connected to the pivot shaft, so that rotation of the screw causes a corresponding rotational movement of the artificial joint to which the flange is connected.

6. The assistive device as recited in claim 1, wherein the first torque profile is greater than the second torque profile, and the first speed profile is less than the second speed profile.

7. The assistive device as recited in claim 1, wherein the transmission mechanism comprises:
the pivot shaft that extends through a longitudinal cutout section of a flange that is connected to the artificial joint;
a leadscrew connected with the pivot shaft, and the leadscrew is connected to a second motor such that the motor is operable to rotate the leadscrew; and
a nut connected to the leadscrew such that rotation of the leadscrew causes the nut to move lengthwise along the leadscrew and change a position of the pivot shaft along the longitudinal cutout section.

8. The assistive device as recited in claim 7, wherein the transmission mechanism is operable to set and fix a position of the pivot shaft with respect to the longitudinal cutout section, and the position of the pivot shaft corresponds to a particular torque profile and speed profile at which the artificial joint is operable.

9. The assistive device as in claim 1, wherein the passively variable element is elastically deformable in response to the power input.

10. The assistive device as recited in claim 1, wherein the power input comprises one or both of a power input from a user and a power input from the motor.

11. The assistive device as recited in claim 1, wherein the passively variable element has a variable length.

12. The assistive device as recited in claim 1, wherein the transmission mechanism comprises a pivot shaft that extends through a longitudinal cutout section of a flange that is connected to the artificial joint, and the passively variable element is connected to the pivot shaft.

13. The assistive device as recited in claim 12, wherein the passively variable element has a first end that is connected to the pivot shaft, and the passively variable element has a second end whose axis of rotation is offset from an axis of rotation of the artificial joint.

14. The assistive device as recited in claim 12, wherein the passively variable element has a first end that is connected to the pivot shaft, and the passively variable element has a second end whose axis of rotation is coincident with an axis of rotation of the artificial joint.

15. The assistive device as recited in claim 1, wherein the passively variable element comprises a damper element.

16. The assistive device as recited in claim 1, further comprising another passively variable element arranged either in series or in parallel with the passively variable element.

17. The assistive device as recited in claim 1, wherein one end of the passively variable element travels either a curved path or a straight path as the passively variable element changes its configuration.

18. The assistive device as recited in claim 1, wherein the artificial joint comprises an artificial human knee joint.

19. The assistive device as recited in claim 1, wherein the assistive device is included in an assistive prosthesis, a powered exoskeleton, or an orthosis device.

20. The assistive device as recited in claim 1, wherein the passively variable element deforms or otherwise changes physical configuration as the crank varies in length between the first crank length and the second crank length.

\* \* \* \* \*